United States Patent
Shelton, IV et al.

(10) Patent No.: US 7,143,925 B2
(45) Date of Patent: Dec. 5, 2006

(54) SURGICAL INSTRUMENT INCORPORATING EAP BLOCKING LOCKOUT MECHANISM

(75) Inventors: Frederick E. Shelton, IV, Hillsboro, OH (US); Eugene L. Timperman, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 11/157,767

(22) Filed: Jun. 21, 2005

(65) Prior Publication Data

US 2006/0022015 A1 Feb. 2, 2006

Related U.S. Application Data

(60) Provisional application No. 60/591,694, filed on Jul. 28, 2004.

(51) Int. Cl.
*A61B 17/068* (2006.01)
(52) U.S. Cl. ............... 227/175.2; 227/175.1; 227/182.1; 227/19
(58) Field of Classification Search ........... 227/175.1, 227/175.2, 182.1, 19
See application file for complete search history.

(56) References Cited

U.S. PATENT DOCUMENTS

| | | | |
|---|---|---|---|
| 5,389,098 A * | 2/1995 | Tsuruta et al. ............ 606/41 |
| 5,441,193 A | 8/1995 | Gravener | |
| 5,465,895 A | 11/1995 | Knodel et al. | |
| 5,503,638 A | 4/1996 | Cooper et al. | |
| 5,542,594 A | 8/1996 | McKean et al. | |
| 5,549,628 A | 8/1996 | Cooper et al. | |
| 5,562,239 A * | 10/1996 | Boiarski et al. ......... 227/175.2 |
| 5,601,582 A * | 2/1997 | Shelton et al. ............ 606/170 |
| 5,665,285 A * | 9/1997 | Hattori et al. ............ 264/45.4 |
| 5,667,517 A * | 9/1997 | Hooven ..................... 606/151 |
| 5,673,840 A | 10/1997 | Schulze et al. | |
| 5,673,841 A | 10/1997 | Schulze et al. | |
| 5,702,409 A | 12/1997 | Rayburn et al. | |
| 5,769,892 A | 6/1998 | Kingwell | |
| 5,779,130 A * | 7/1998 | Alesi et al. ............ 227/176.1 |
| 5,797,537 A | 8/1998 | Oberlin et al. | |

(Continued)

FOREIGN PATENT DOCUMENTS

EP    0 832 605    4/1998

(Continued)

OTHER PUBLICATIONS

EPO Search Report, Application No. 05254680.1, Jan. 12, 2006, pp. 1-5.

(Continued)

*Primary Examiner*—John Sipos
*Assistant Examiner*—Michelle Lopez

(57) ABSTRACT

A surgical stapling and severing instrument particularly suited to endoscopic procedures incorporates a handle that produces separate closing and firing motions to actuate an end effector. The handle produces multiple firing strokes to reduce the required amount of force required to fire (i.e., staple and sever) the end effector. A linked transmission reduces the required handle longitudinal length, yet achieves a rigid, strong configuration when straightened for firing. One or more electrically activated lockout mechanisms, such as electroactive polymer (EAP) actuators, are biased to prevent firing unless activated. One lockout is a spring-biased side pawl firing mechanism enabled by an EAP block actuator. Another is a firing trigger EAP lock. Yet another is a closure yoke EAP lock. Yet a further one is a manual retraction EAP lock that locks the firing mechanism. Thereby, various sensed or commanded inputs may be incorporated to prevent inadvertent firing.

6 Claims, 27 Drawing Sheets

U.S. PATENT DOCUMENTS

| | | | |
|---|---|---|---|
| 5,810,855 | A | 9/1998 | Rayburn et al. |
| 5,865,361 | A | 2/1999 | Milliman et al. |
| 5,902,312 | A | 5/1999 | Frater et al. |
| 5,908,427 | A | 6/1999 | McKean et al. |
| 5,964,774 | A | 10/1999 | McKean et al. |
| 6,063,097 | A | 5/2000 | Oi et al. |
| 6,503,257 | B1 | 1/2003 | Grant et al. |
| 6,652,521 | B1 * | 11/2003 | Schulze ............... 606/45 |
| 6,656,193 | B1 | 12/2003 | Grant et al. |
| 6,667,825 | B1 | 12/2003 | Lu et al. |
| 6,835,173 | B1 | 12/2004 | Couvillon, Jr. |
| 7,044,352 | B1 * | 5/2006 | Shelton et al. ........... 227/175.1 |
| 7,063,699 | B1 * | 6/2006 | Hess et al. ............... 606/51 |
| 2002/0165541 | A1 * | 11/2002 | Whitman ............... 606/48 |
| 2003/0065358 | A1 | 4/2003 | Frecher |
| 2003/0069474 | A1 | 4/2003 | Couvillion et al. |
| 2003/0199870 | A1 * | 10/2003 | Truckai et al. ........... 606/51 |
| 2004/0232196 | A1 | 11/2004 | Shelton et al. |
| 2004/0232197 | A1 | 11/2004 | Shelton et al. |
| 2005/0006434 | A1 | 1/2005 | Wales et al. |
| 2005/0067457 | A1 | 3/2005 | Shelton et al. |
| 2005/0067458 | A1 | 3/2005 | Swayze et al. |
| 2005/0173490 | A1 * | 8/2005 | Shelton, IV ............. 227/175.2 |

FOREIGN PATENT DOCUMENTS

| | | |
|---|---|---|
| EP | 1 522 264 | 4/2005 |
| WO | WO 99/02090 | 1/1999 |
| WO | WO 03/094743 | 11/2003 |
| WO | WO 2004/050971 | 6/2004 |

OTHER PUBLICATIONS

EPO Search Report, Application No. 05254694.2, Jan. 12, 2006, pp. 1-5.

EPO Search Report, Application No. 05254685.0, Jan. 12, 2006, pp. 1-5.

EPO Search Report, Application No. 05254695.9, Jan. 12, 2006, pp. 1-5.

* cited by examiner

SURGICAL INSTRUMENT INCORPORATING EAP BLOCKING LOCKOUT MECHANISM

CROSS REFERENCE TO RELATED APPLICATIONS

This application claims the benefit of U.S. provisional application Ser. No. 60/591,694, entitled "SURGICAL INSTRUMENT INCORPORATING AN ELECTRICALLY ACTUATED ARTICULATION MECHANISM" to Shelton IV, filed 28 Jul. 2004.

FIELD OF THE INVENTION

The present invention relates in general to surgical stapler instruments that are capable of applying lines of staples to tissue while cutting the tissue between those staple lines and, more particularly, to improvements relating to stapler instruments and improvements in processes for forming various components of such stapler instruments that preclude inadvertent firing.

BACKGROUND OF THE INVENTION

Laparoscopic and endoscopic ("minimally invasive") surgical instruments are often preferred over traditional open surgical devices since a smaller incision tends to reduce the post-operative recovery time and complications. Consequently, significant development has gone into a range of minimally invasive surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

These devices often perform a mechanical surgical action upon tissue, such as grasping, anastomosis, cutting, stapling, etc. A reliable approach is to mechanically implement such a capability through the limited confines of the elongate shaft. Much development has gone into integrating one or more motions through the handle and shaft to realize successful instruments.

For instance, surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

Avoiding even extremely rare instances of equipment malfunction or human error is a highly desirable goal for minimally invasive instruments. To that end, many mechanical lockouts have been introduced. For instance, with regard to surgical staplers, it is known to mechanically lockout firing if a spent cartridge is present in the end effector or the end effector is not closed and clamped.

While such lockout mechanisms have certain advantages, it is desirable in some instances to provide an alternative or an additional lockout mechanism. Elaborate mechanical implementations often pose design challenges and introduce additional sources of failure or user complexity.

Consequently, a significant need exists for an improved surgical instrument that prevents inadvertent actuation.

BRIEF SUMMARY OF THE INVENTION

The invention overcomes the above-noted and other deficiencies of the prior art by providing a surgical stapling and severing instrument that advantageously incorporates an electrically actuated lockout mechanism in a handle that prevents actuation through an elongate shaft to an end effector. Insofar as an electrical actuator is biased toward locking out, a plurality of undesirable conditions for actuation may be avoided.

In one aspect of the invention, a surgical instrument that includes an end effector of opposing jaws is advantageously locked out by an electroactive polymer (EAP) actuator that is biased to lock a proximal actuator preventing closing of the jaws. Thereby, undesirable use of the instrument (e.g., insertion through a trocar, subsequent firing after closing) is avoided by this lockout.

In another aspect of the invention, a surgical instrument has a firing member that actuates an end effector that is a staple applying apparatus having a lower jaw and pivotally attached upper jaw. An electrically powered actuator locks to a proximal actuator that is coupled to the firing member to prevent firing in certain situations.

These and other objects and advantages of the present invention shall be made apparent from the accompanying drawings and the description thereof.

DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

Figure 1:
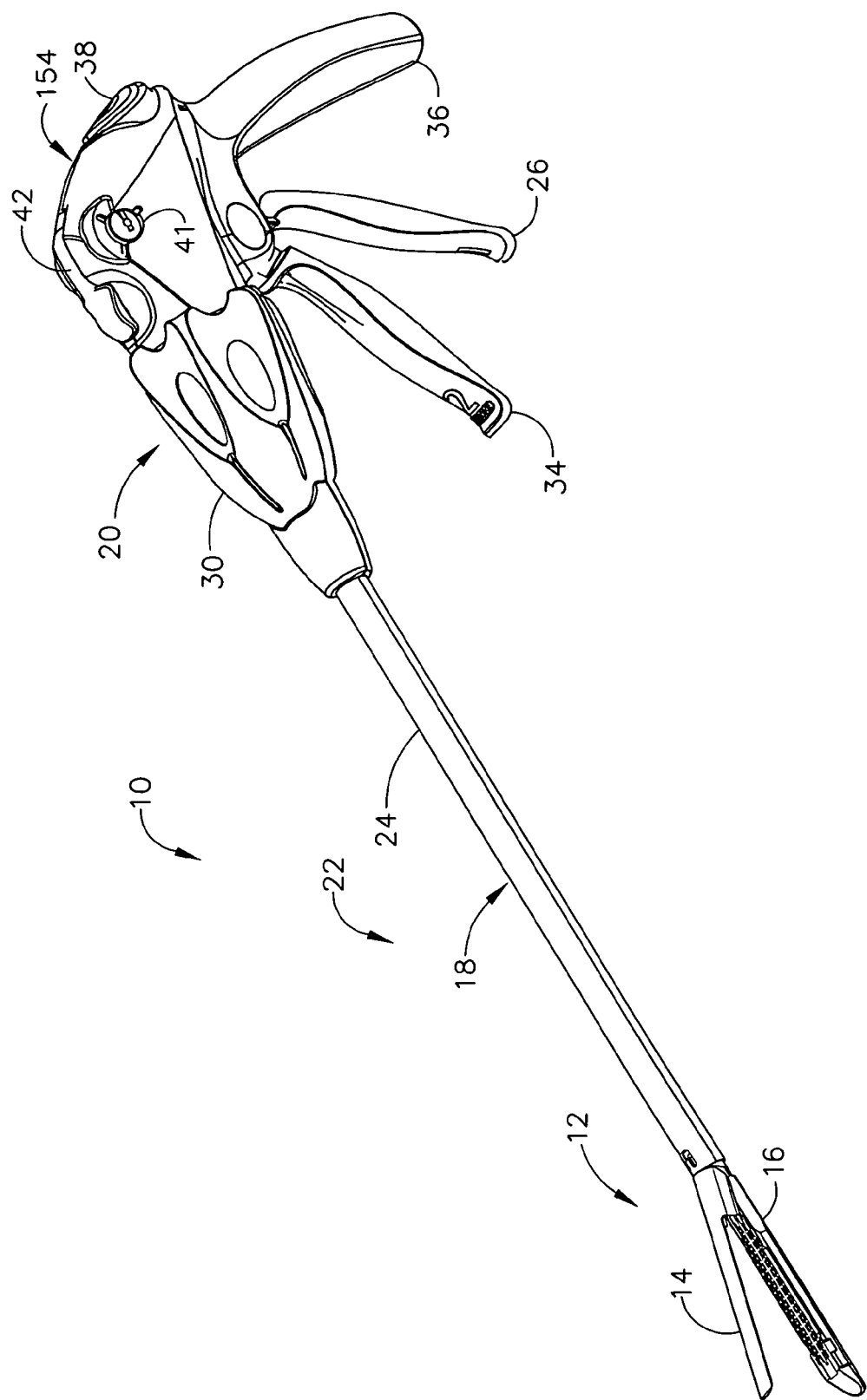
FIG. 1 is a left front perspective view of a surgical stapling and severing instrument incorporating an Electroactive Polymer (EAP) blocking, complete lockout mechanism in a handle portion.

In FIG. 1, a surgical stapling and severing instrument 10 includes multi-stroke firing of an end effector, which in the illustrative version is a staple applying apparatus 12. An anvil 14 may be repeatably opened and closed about its pivotal attachment to an elongate (staple) channel 16. The staple applying assembly 12 is proximally attached to elongate shaft 18, forming an implement portion 22. When the staple applying assembly 12 is closed, the implement portion 22 presents a small cross-sectional area suitable for insertion through a cannula of a trocar by manipulating handle 20, which is attached to a proximal end of elongate shaft 18.

The handle 20 has user controls mounted on its handle housing 154 user controls such as a rotation knob 30 that rotates the elongate shaft 18 and staple applying assembly 12 about a longitudinal axis of the shaft 18. A closure trigger 26, which pivots in front of a pistol grip 36 about a closure trigger pin 152 (FIGS. 2–5) and is engaged laterally across the handle housing 154, is depressed to close the staple applying assembly 12. A multiple stroke firing trigger 34, which pivots in front of the closure trigger 26, causes the staple applying assembly 12 to simultaneously sever and staple tissue clamped therein. Since multiple firing strokes are employed to reduce the amount of force required per stroke by the surgeon's hand, right and left indicator gauge wheels 40, 41 (the former depicted in FIG. 3) rotate presenting indicia of the firing progress. For instance, full firing travel may require three full firing strokes and thus the indicator wheels 40, 41 rotate up to one-third of a revolution each per stroke. A manual firing release lever 42 allows retraction before full firing travel if desired and allows assistance to retract in the presence of binding or a failure in the retraction bias. A closure release button 38 is outwardly presented when the closure trigger 26 is clamped and partial firing has not occurred that would prevent unclamping the closure trigger 26.

Figure 2:
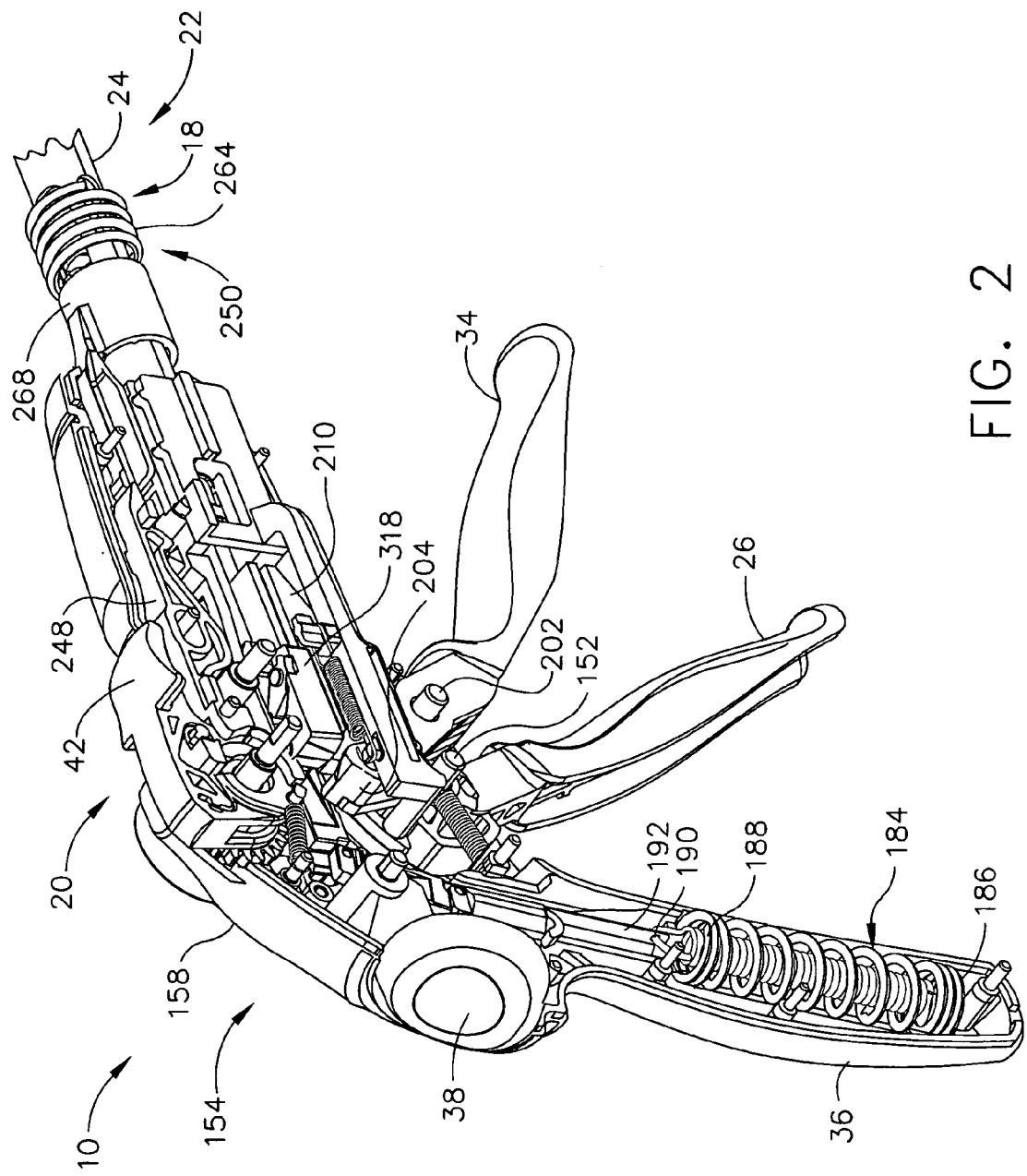
FIG. 2 is a right aft perspective view of the handle portion of the surgical stapling and severing instrument of FIG. 1 with a right half shell of a handle housing removed to expose closure and firing mechanisms.
Figure 3:
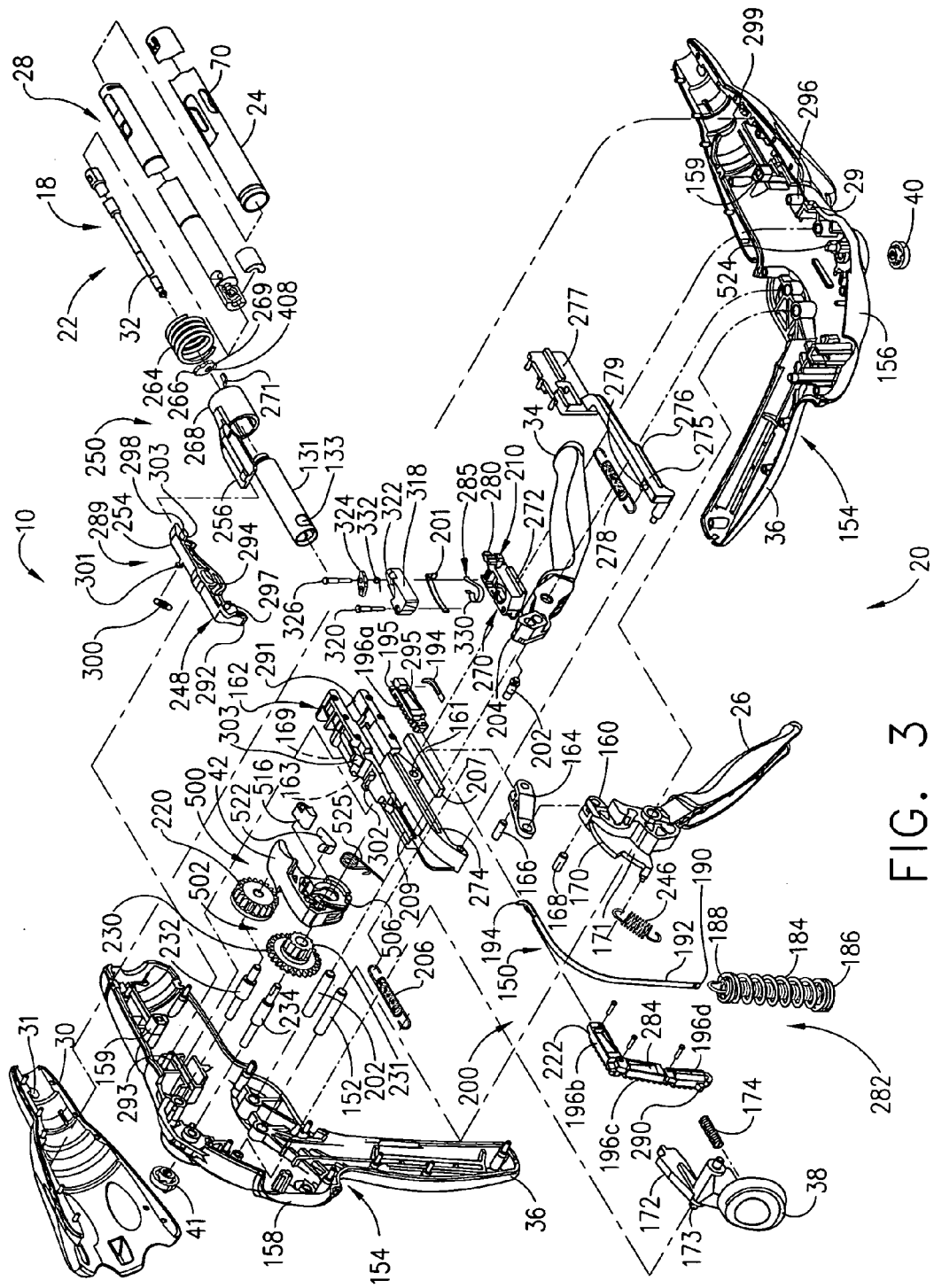
FIG. 3 is a right aft perspective disassembled view of the handle portion and an elongate shaft of the surgical stapling and severing instrument of FIG. 1.

With reference to FIGS. 1–5, the elongate shaft 18 has as its outer structure a longitudinally reciprocating closure tube 24 that pivots the anvil 14 (FIG. 1) to effect closure in response to proximal depression of the closure trigger 26 of the handle 20. With particular reference to FIG. 3, the elongate channel 18 is connected to the handle 20 by a frame 28 that is internal to the closure tube 24. The frame 28 is rotatably engaged to the handle 20 so that twisting the rotation knob 30 causes rotation of the implement portion 22. Each half shell of the rotation knob 30 includes an inward projection 31 that enters a respective longer side opening 70 in the closure tube 24 and projects further inward to engage the frame 28 to transfer the rotation of the rotation knob 30 to the implement portion 22. The longitudinal length of the side opening 70 is sufficiently long to allow longitudinal closure motion of the closure tube 24 with the inward projection 31 remaining longitudinally at a fixed distance.

In FIG. 3, an upper portion 160 of the closure trigger 26 pushes forward a closure yoke 162 via a closure link 164. The closure link 164 is pivotally attached at its distal end by a closure yoke pin 166 to the closure yoke 162 at attachment point 161 and is pivotally attached at its proximal end by a closure link pin 168. The closure trigger 26 is urged to the open position by a closure trigger tension spring 246 that is connected proximally to the upper portion 160 of the closure trigger 26 and to the handle housing 154 formed by right and left half shells 156, 158. The right and left half shells 156, 158 each include a closure yoke guide post 159 (FIGS. 3, 4) that slides with a horizontally elongate rectangular aperture 169 formed in a left side of the closure yoke 162, with the post 159 at a distal position in the aperture 169 as in FIG. 4 when the closure yoke 162 is proximally positioned with anvil 14 open.

Figure 4:
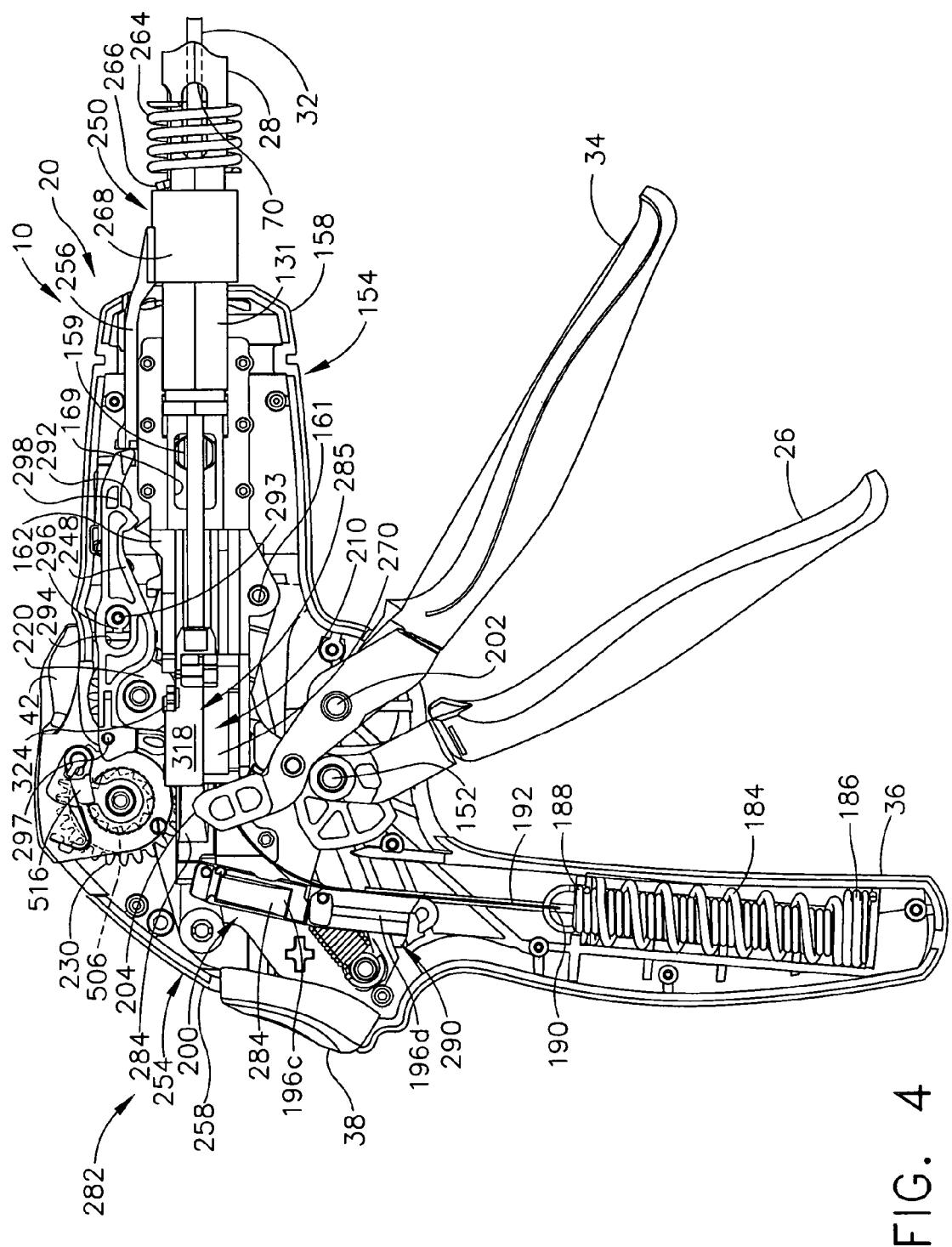
FIG. 4 is right side view of the surgical stapling and severing instrument of FIG. 1 with a right half shell and distal portions of the implement portion removed to expose the closure and firing mechanisms in an initial state.

The upper portion 160 of the closure trigger 26 includes a proximal crest 170 with an aft notch 171. The closure release button 38 and a pivoting locking arm 172 are connected by a central lateral pivot 173. A compression spring 174 biases the closure release button 38 proximally (clockwise about the central lateral pivot 173 as viewed from the right), With the upper portion 160 back when the closure trigger 26 is released as depicted in FIGS. 2, 4, the pivoting locking arm 172 rides upon the proximal crest 170 drawing in the closure release button 38. When the closure trigger 26 reaches its fully depressed position, it should be appreciated that the aft notch 171 is presented below the pivoting locking arm 172, which drops into and locks against the aft notch 171 under the urging of the compression spring 174. With the firing components retracted, manual depression of the closure release button 38 rotates the pivoting locking arm 172 upward unclamping the closure trigger 26.

Once the closure trigger 26 is proximally clamped, a firing rod 32 is distally moved from the handle 20 in response to the multiple stroke firing trigger 34 being drawn to the pistol grip 36 with the amount of firing travel visible to the surgeon on right and left indicator gauge wheels 40, 41. The firing trigger 34 pivots about a firing trigger pin 202 that laterally traverses and is engaged to the right and left half shells 156, 158.

A linked transmission firing mechanism 150 is initially retracted, urged to remain in this position by the combination tension/compression spring 184 that is constrained within the pistol grip 36 of the handle 20, with its nonmoving end 186 connected to a housing 154 and a moving end 188 connected to a downwardly flexed and proximal, retracted end 190 of a steel band 192.

A distally-disposed end 194 of the steel band 192 is attached to an attachment feature 195 on a front link 196a of a plurality of links 196a–1196d that form a linked rack 200. Linked rack 200 is flexible yet has distal links that form a straight rigid rack assembly that may transfer a significant firing force through the firing rod 32 in the implement portion 22, yet readily retracts into the pistol grip 36 to minimize the longitudinal length of the handle 20. It should be appreciated that the combination tension/compression spring 184 increases the amount of firing travel available while essentially reducing the minimum length by half over a single spring.

Anti-Backup Mechanism.

Figure 5:
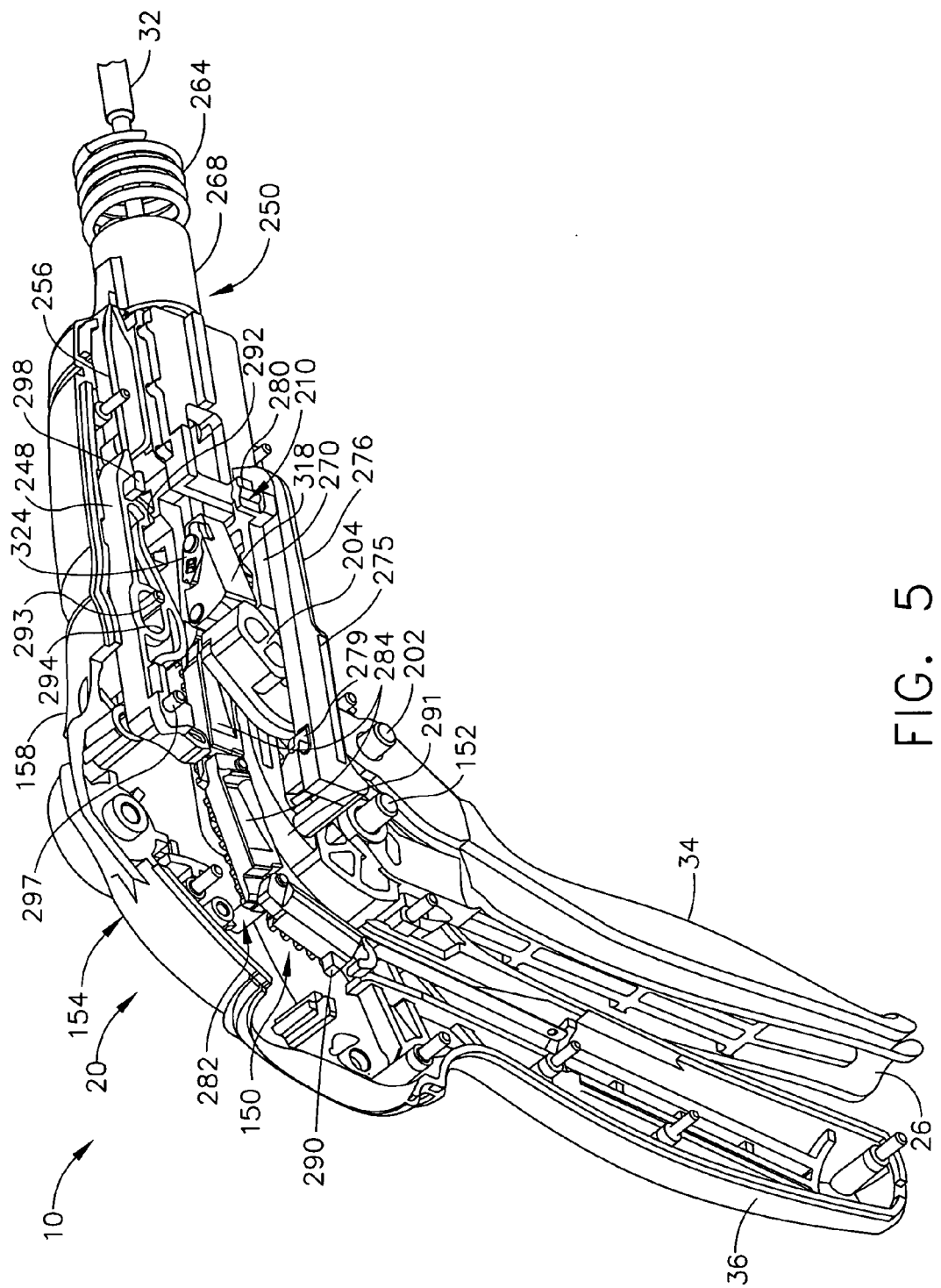
FIG. 5 is a right aft perspective view of the partially disassembled surgical stapling and severing instrument of FIG. 4 with a closure mechanism closed and clamped and a side pawl firing mechanism completing a first stroke and with a manual retraction mechanism removed to expose a distal link of the linked rack that triggers automatic retraction of the firing mechanism.

In FIGS. 3–5, an anti-backup mechanism 250 prevents the combination tension/compression spring 184 from retracting the linked rack 200 between firing strokes. A coupling tube 131 proximally distally connects to the firing rod 32 to communicate the firing motion. The guide posts 159 engage lateral recesses 133 on a proximal portion of coupling slide tube 131. Links 196a and 196b enter a proximally open cavity in the coupling tube 131 when fired. The firing rod 32 extends proximally out of a proximal end of the frame 28 and through a through hole 408 of an anti-backup plate 266. The through hole 408 is sized to slidingly receive the firing rod 32 when perpendicularly aligned but to bind when tipped. A lower tab attachment 271 extends proximally from a lower lip of the proximal end of the frame 28, extending through an aperture 269 on a lower edge of the anti-backup plate 266. This lower tab attachment 271 draws the lower portion of the anti-backup plate 266 proximate to the frame 28 so that the anti-backup plate 266 is perpendicular when the firing rod 32 is distally advanced and allowed to tip top aft into a binding state when the firing rod 32 attempts to retract. An anti-backup compression spring 264 is distally constrained by the proximal end of the frame 28 and proximally abutts a top portion of the anti-backup plate 266, biasing the anti-backup plate 266 to a locking state.

Opposing the spring bias, an anti-backup cam tube 268 slidingly encompasses the coupling tube 131 and abuts the anti-backup plate 266. A proximally projecting anti-backup yoke 256 attached to the anti-backup cam tube 268 extends overtop of the closure yoke 162.

Linked Rack Triggered Automatic Retraction.

In FIGS. 1–5, a link triggered automatic retraction mechanism 289 is incorporated into the surgical stapling and severing instrument 10 to cause knife retraction at the end of full firing travel. To that end, the most proximal link 196d includes a tang 290 that projects upwardly when the most proximal link 196d is advanced into rack channel 291 formed in the closure yoke 162. This tang 290 is aligned to activate a bottom proximal cam 292 on an anti-backup release lever 248. Structures formed in the right and left half shells 156, 158 constrain movement of the anti-backup release lever 248. A pin receptacle 296 and circular pin 293, formed respectively inside right and left half shells 156, 158, is received through a longitudinally elongate aperture 294 formed in the anti-backup release lever 248 distal to the bottom proximal cam 292, thus allowing longitudinal translation as well as rotation about the circular pin 293 and pin receptacle 296. In the right half shell 156, a proximally open channel 295 includes a proximal horizontal portion that communicates with an upwardly and distally angled portion that receives a rightward aft pin 297 near the proximal end of the anti-backup release lever 248, thus imparting an upward rotation as the anti-backup release lever 248 reaches the distal most portion of its translation. A blocking structure, formed in the right half shell 156 proximal to the anti-backup release lever 248, prevents proximal movement thereof once assembled to maintain rightward aft pin 297 in the proximally open channel 295.

A distal end 254 of the anti-backup release lever 248 thus is urged distally and downwardly, causing a rightward front pin 298 to drop into distally open step structure 299 formed in the right half shell 156, which is urged into this engagement by a compression spring 300 hooked to a leftward hook 301 on the anti-backup release lever 248 between the rightward front pin 298 and the longitudinally elongate aperture 294. The other end of the compression spring 300 is attached to a hook 302 mounted on the top surface of closure yoke 162. The compression spring 300 thus pulls the distal end 254 of the anti-backup release lever 248 down and aft, which results in the rightward front pin 298 locking into the distally open step structure 299 when distally advanced.

Once tripped, the anti-backup release lever 248 remains forward holding the anti-backup plate 266 perpendicularly, thus allowing the linked rack 200 to be retracted. When the closure yoke 162 is subsequently retracted when unclamping the end effector 12, an upwardly projecting reset tang 303 on the closure yoke 162 contacts a bottom distal cam 305 of the anti-backup release lever 248, lifting the rightward front pin 298 out of the distally open step structure 299 so that the anti-backup compression spring 264 can proximally push the anti-backup cam tube 268 and the anti-backup release lever 248 to their retracted positions.

Side Pawl Firing Mechanism Incorporating EAP Lockout Mechanism.

Figure 6:
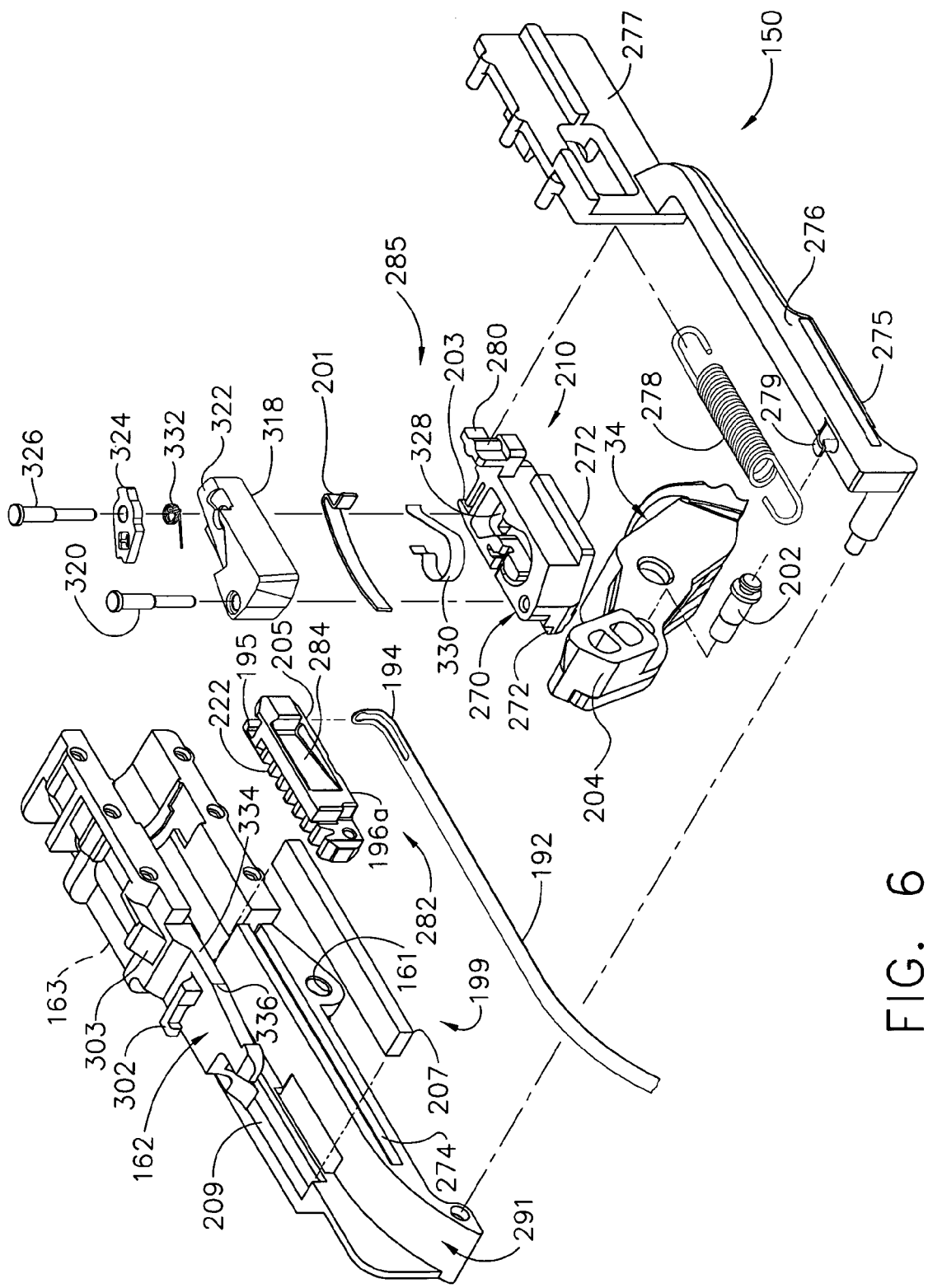
FIG. 6 is a detail right aft disassembled perspective view of a linked rack firing mechanism of FIG. 3 formed from a closure yoke assembly and the side pawl firing mechanism with an EAP lockout mechanism.
Figure 7:
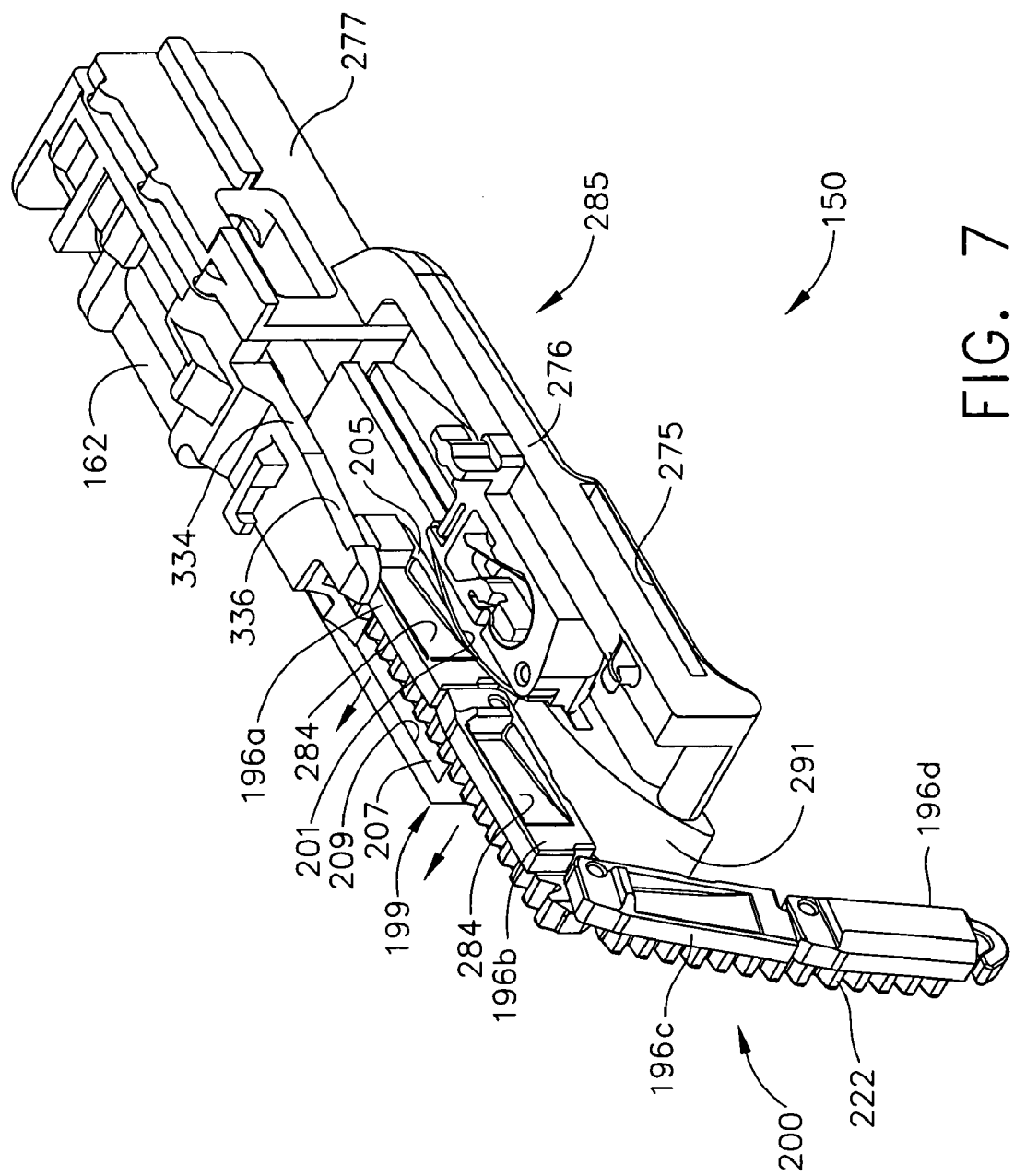
FIG. 7 is a right aft perspective view of the linked rack firing mechanism of FIG. 6 depicted with a proximally retracted linked rack and a side pawl firing mechanism with the EAP lockout mechanism disengaged (electrically inactivated).
Figure 8:
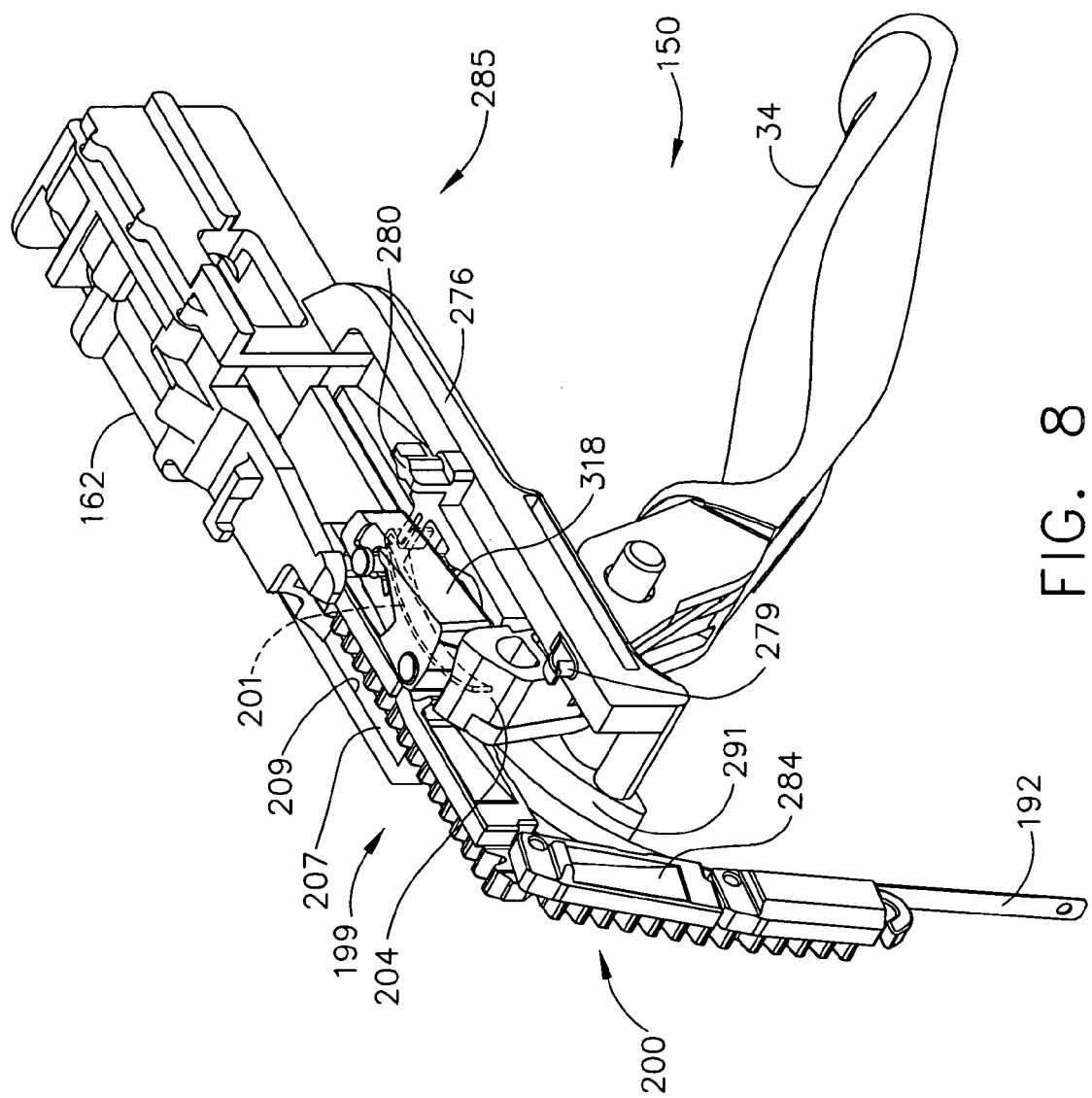
FIG. 8 is a right aft perspective view of the linked rack firing mechanism including a portion of the side pawl assembly of FIG. 7 with the addition of a firing trigger and pawl block with a bumper spring shown in phantom.
Figure 9:
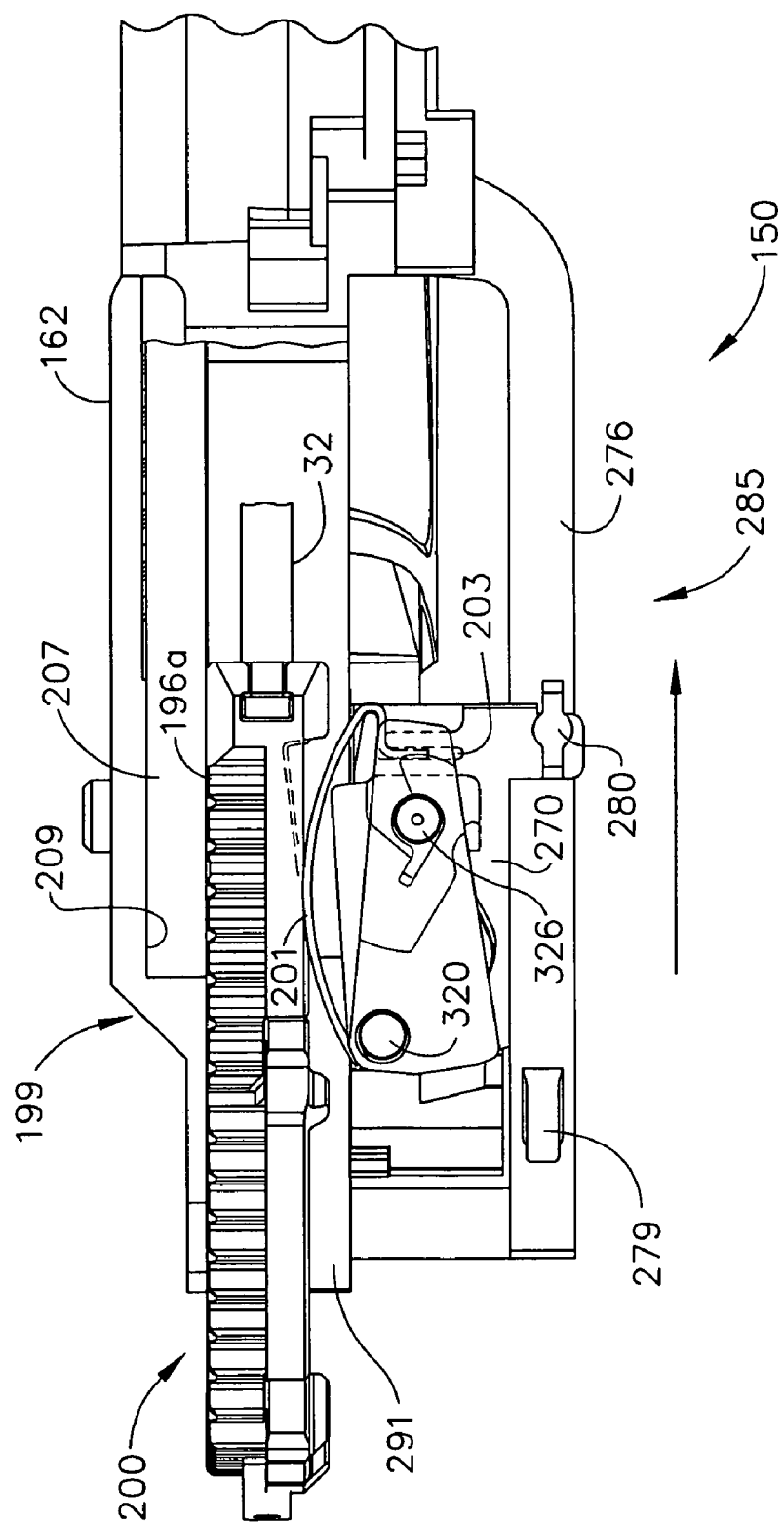
FIG. 9 is a top view of the linked rack firing mechanism including a portion of the side pawl assembly of FIG. 8 with the further addition of a kick-out block on the pawl block.

The handle 20, especially the linked rack firing mechanism 150, is described in greater detail in the commonly-owned U.S. patent application Ser. No. 11/052,387, hereby incorporated by reference in its entirety, such as depictions of a side pawl assembly intermittently driving a linked rack. With particular reference to FIG. 6, however, a side pawl assembly 285 is modified to include an EAP lockout mechanism 199. In particular, modifications to the linked rack firing mechanism 150, specifically the closure yoke 162, pawl slide (shuttle) 270, and links 196a–d, allow a bumper spring 201 to be distally gripped in a curved vertically open slot 203 in the pawl slide 270, extending a proximal bowed portion along the left side of the pawl slide 270. Each link 196a–d has a horizontal recess 205 along the bottom of its right side to present an uninterrupted contact surface to the bumper spring 201 to receive a leftward bias therefrom, moving the linked rack 200 out of engagement. An EAP block actuator 207 retained in a rightwardly open horizontal slot 209 in the closure yoke 162, when activiated against the right side of the links 196a–d, urges the linked rack 200 into close proximity to the pawl slide 270, compressing the bumper spring 201, thereby enabling firing.

It should be appreciated that a number of control circuitry features may thus be incorporated to prevent firing. For example, an enabling switch may be added to the handle 20. As another example, sensors in the end effector 12 may be included, such as presence or absence of an unspent staple cartridge, and presence of an appropriate amount of tissue clamped into the end effector, presence or absence of ancillary compounds or therapeutic features (e.g., a cauterizing, sterilizing, etc.). Futher, control circuitry may comprise lumped analog components, a programmable logic array, a microcontroller, or other types of electronic circuits.

Electroactive Polymers.

Electroactive polymers (EAPs) are a set of conductive doped polymers that change shape when electrical voltage is applied. In essence, the conductive polymer is paired to some form of ionic fluid or gel and electrodes. Flow of the ions from the fluid/gel into or out of the conductive polymer is induced by the voltage potential applied and this flow induces the shape change of the polymer. The voltage potential ranges from 1V to 4 kV, depending on the polymer and ionic fluid used. Some of the EAPs contract when voltage is applied and some expand. The EAPs may be paired to mechanical means such as springs or flexible plates to change the effect that is caused when the voltage is applied.

There are two basic types and multiple configurations of each type. The two basic types are a fiber bundle and a laminate version. The fiber bundle consists of fibers around 30–50 microns. These fibers may be woven into a bundle much like textiles and are often called EAP yarn because of this. This type of EAP contracts when voltage is applied. The electrodes are usually a central wire core and a conductive outer sheath, which also serve to contain the ionic fluid that surrounds the fiber bundles. An example of a commercially available fiber EAP material is manufactured by Santa Fe Science and Technology, sold as PANION fiber and described in U.S. Pat. No. 6,667,825, which is hereby incorporated by reference in its entirety.

The other type is a laminate structure. It consists of a layer of EAP polymer, a layer of ionic gel and two flexible plates that are attached to either side of the laminate. When a voltage is applied, the square laminate plate expands in one direction and contracts in the perpendicular direction. An example of a commercially available laminate (plate) EAP material is available from Artificial Muscle Inc, a division of SRI Laboratories. Plate EAP material is also available from EAMEX of Japan and referred to as thin film EAP.

It should be noted that EAPs do not change volume when energized; they merely expand or contract in one direction while doing the opposite in the transverse direction. The laminate version may be used in its basic form by containing one side against a rigid structure and using the other much like a piston. It may also be adhered to either side of a flexible plate. When one side of the flexible plate EAP is energized it would expand, flexing the plate in the opposite direction. This allows the plate to be flexed either direction depending on which side is energized.

An EAP actuator usually consists of numerous layers or fibers bundled together to work in cooperation. The mechanical configuration of the EAP determines the EAP actuator and its capabilities for motion. The EAP may be formed into long stands and wrapped around a single central electrode. A flexible exterior outer sleeve will form the other electrode for the actuator as well as contain the ionic fluid necessary for the function of the device. In this configuration when the electrical field is applied to the electrodes, the strands of EAP shorten. This configuration of the EAP actuator is called a fiber EAP actuator. Likewise, the laminate configuration may be placed in numerous layers on either side of a flexible plate or merely in layers on itself to increase its capabilities. Typical fiber structures have an effective strain of 2–4% where the typical laminate version achieves 20–30%, utilizing much higher voltages. It should be appreciated, however, that these performance ranges are not determinative.

For instance, a laminate EAP composite may be formed from a positive plate electrode layer attached to an EAP layer, which in turn is attached to an ionic cell layer, which in turn is attached to a negative plate electrode layer. A plurality of laminate EAP composites may be affixed in a stack by adhesive layers therebetween to form an EAP plate actuator. It should be appreciated that opposing EAP actuators may be formed that can selectively bend in either direction.

A contracting EAP fiber actuator may include a longitudinal platinum cathode wire that passes through an insulative polymer proximal end cap, and then through an elongate cylindrical cavity formed within a plastic cylinder wall that is conductively doped to serve as a positive anode. A distal end of the platinum cathode wire is embedded into an insulative polymer distal end cap. A plurality of contracting polymer fibers are arranged parallel with and surrounding the cathode wire and have their ends embedded into respective end caps. The plastic cylinder wall is peripherally attached around respective end caps to enclose the cylindrical cavity to seal in ionic fluid or gel that fills the space between contracting polymer fibers and cathode wire. When a voltage is applied across the plastic cylinder wall (anode) and cathode wire, ionic fluid enters the contracting polymer fibers, causing their outer diameter to swell with a corresponding contraction in length, thereby drawing the end caps toward one another.

Firing and Automatic Retraction.

With particular reference to FIGS. 2–5, the firing trigger 34 pivots about a firing trigger pin 202 that is connected to the housing 154. A firing actuator, depicted as an upper portion 204 of the firing trigger 34, moves distally about the firing trigger pin 202 as the firing trigger 34 is depressed toward pistol grip 36, stretching a proximally placed firing trigger tension spring 206 (FIG. 3) proximally connected between the upper portion 204 of the firing trigger 34 and the housing 154. The upper portion 204 of the firing trigger 34 engages the linked rack 200 during each firing trigger depression by a spring-biased side pawl mechanism 210 that also disengages when the firing trigger 34 is released.

In particular, a ramped right-side track 282 formed by a proximally and rightwardly facing beveled surface 284 in each of the links 196a–196d is engaged by a side pawl assembly 285. In particular, the pawl slide (shuttle) 270 (FIGS. 3, 6) has right and left lower guides 272 that slide respectively in a left track 274 (FIGS. 3, 6) formed in the closure yoke 162 below the rack channel 291 and a right track 275 in a closure yoke rail 276 that parallels rack channel 291 and is attached to a rack channel cover 277 that closes a rightwardly open portion of the rack channel 291 in the closure yoke 162 that is distal to the travel of the pawl slide 270. In FIGS. 3, 6, a compression spring 278 is attached between a hook 279 on a top proximal position on the closure yoke rail 276 and a hook 280 on a distal right side of the pawl slide 270, which keeps the pawl slide 270 drawn proximally into contact with the upper portion 204 of the firing trigger 34. The other depictions omit the compression spring 278 for clarity.

With particular reference to FIG. 6, a pawl block 318 sits on the pawl slide 270 pivoting about a vertical aft pin 320 that passes through a left proximal corner of pawl block 318 and pawl slide 270. A kick-out block recess 322 is formed on a distal portion of a top surface of the block 318 to receive a kick-out block 324 pivotally pinned therein by a vertical pin 326 whose bottom tip extends into a pawl spring recess 328 on a top surface of the pawl slide 270. A pawl spring 330 in the pawl spring recess 328 extends to the right of the vertical front pin 326, urging the pawl block 318 to rotate counterclockwise when viewed from above into engagement with the ramped right-side track 282. A small coil spring 332 in the kick-out block recess 322 urges the kick-out block 324 to rotate clockwise when viewed from above, its proximal end urged into contact with a contoured lip 334 formed in the closure yoke 162 above the rack channel 291.

Figure 10:
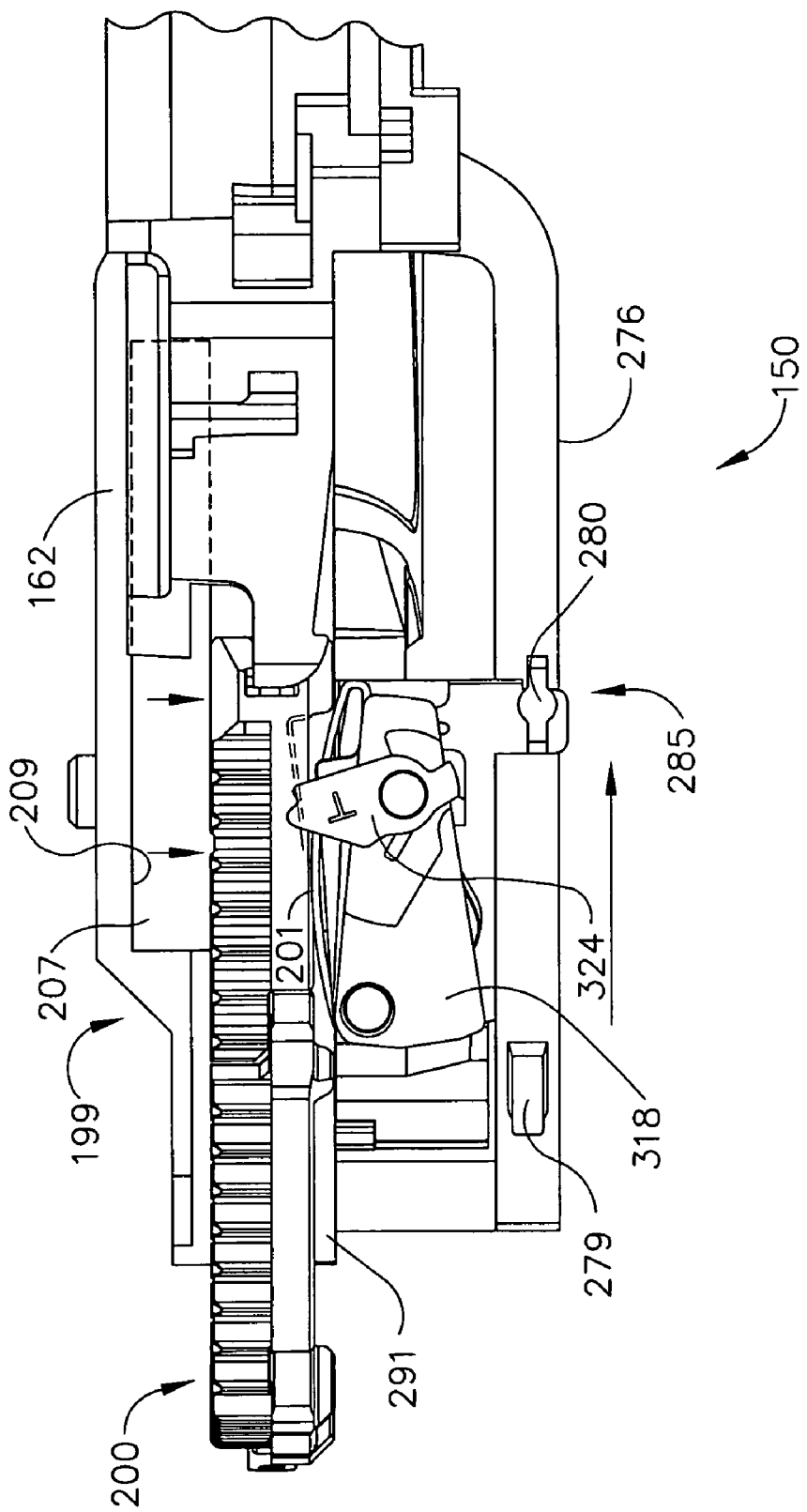
FIG. 10 is a top view of the linked rack firing mechanism of FIG. 9 with the EAP lockout mechanism activated, shifting the linked rack to the right into engagement with the pawl block and kick-out block.
Figure 11:
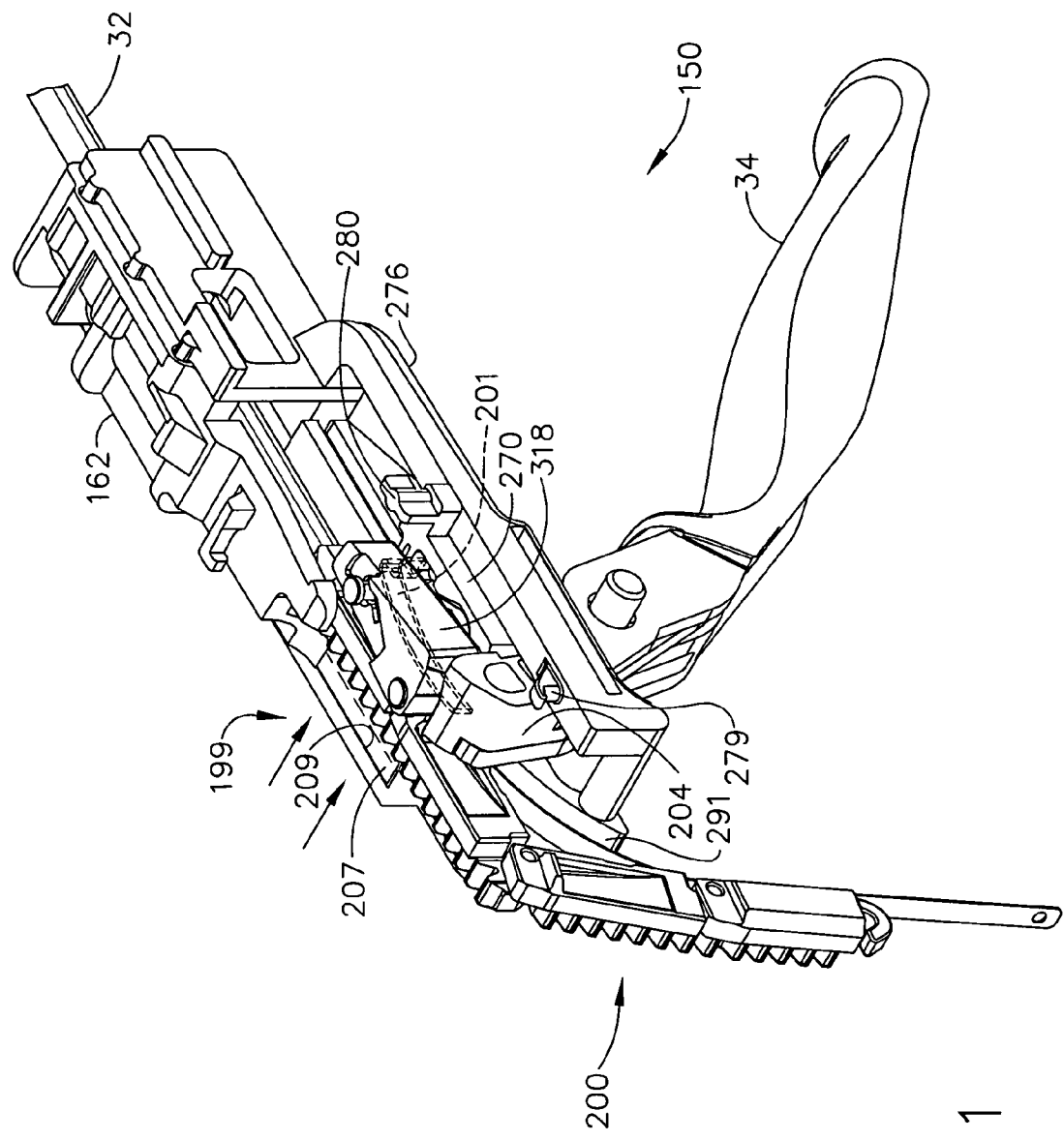
FIG. 11 is a right aft perspective view of the linked rack firing mechanism including the side pawl assembly, linked rack, closure yoke and rail, and firing trigger with the EAP lockout mechanism activated enabling firing.
Figure 12:
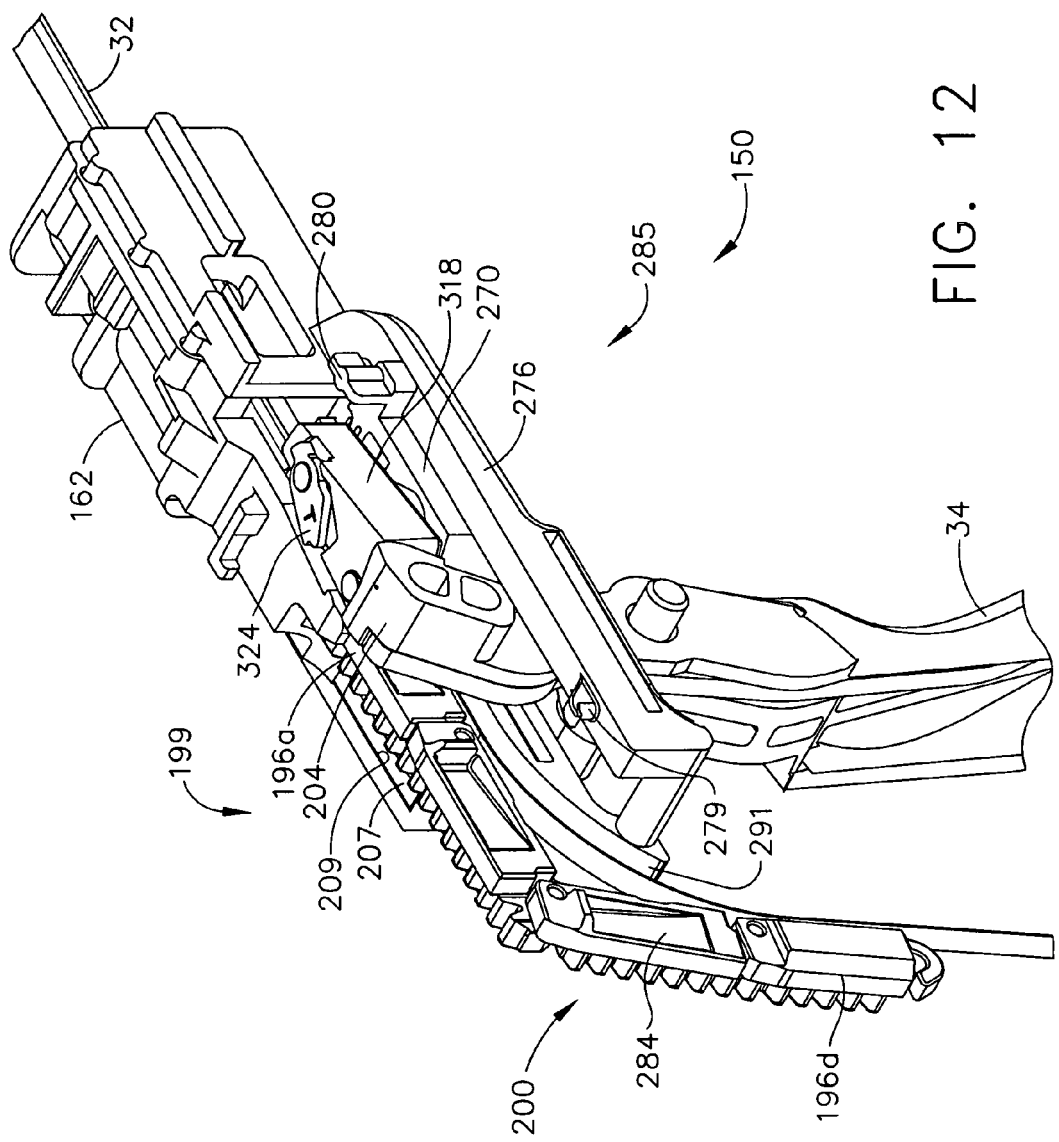
FIG. 12 is a right aft perspective view of the linked rack firing mechanism of FIG. 11 after a firing stroke with the EAP lockout mechanism inactivated, preventing advancement of the linked rack.

The stronger mechanical advantage of the pawl spring 330 over the small coil spring 332 means that the pawl block 318 tends toward engagement with the kick-out block 324 rotated clockwise. In FIG. 5, as the firing trigger 34 is fully depressed and begins to release, the kick-out block 324 encounters a ridge 336 in the contoured lip 334 as the pawl slide 270 retracts, forcing the kick-out block 324 to rotate clockwise when viewed from above and thereby kicking out the pawl block 318 from engagement with the linked rack 200. The shape of the kick-out block recess 322 stops the clockwise rotation of the kick-out block 324 to a perpendicular orientation to the contoured lip 334 (FIG. 10), maintaining this disengagement during the full retraction and thereby eliminating a ratcheting noise.

With the exception of modifications described above to incorporate the afore-described EAP lockout mechanism 150, the handle 20 is described in greater detail in two commonly-owned U.S. patent application Ser. Nos. 11/052,387 and 11/052,632, both filed on 7 Feb. 2005, the disclosures of both of which are hereby incorporated by reference in their entirety.

Operation of the EAP Firing Pawl Lockout Mechanism.

In FIGS. 7–12, the side pawl assembly 285 is depicted in operation performing locking out of firing. In particular, in FIGS. 7–9, the pawl slide 270 is laterally constrained by being longitudinally guided between the closure yoke 162 and the closure yoke rail 276. The bumper spring 201 extends laterally to the left of the pawl slide 270 against the horizontal recess 205 of an adjacent link 196a of the linked rack 200, urging the linked rack 200 to the left across the rack channel 291 formed in the closure yoke 162. The EAP block actuator 207 is laterally contracted in a deactivated state, confined within the rightwardly open horizontal slot 209 in the closure yoke 162. Thus, with the firing trigger 34 drawn from its relaxed position (FIG. 8) to its depressed position (FIG. 12), the top portion 204 of the firing trigger 34 advances the pawl slide 270 without the pawl block 318 engaging the proximally and rightwardly facing beveled surface 284 of the link 196a. Thus, no force is imparted to the linked rack 200 that would have to be blocked downstream in the event of an undesirable firing condition.

Closure EAP Blocking Lockout.

Figure 13:
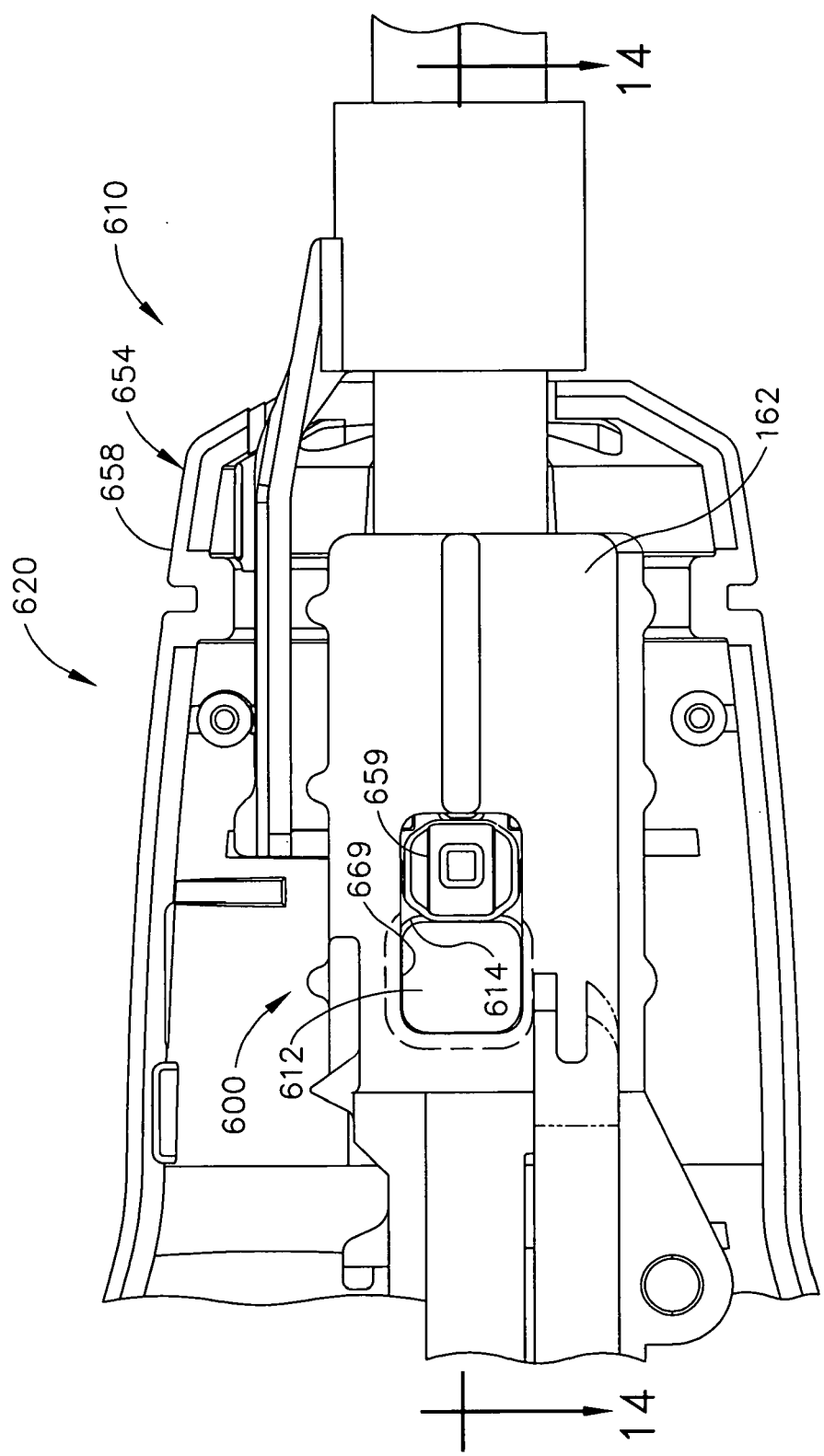
FIG. 13 is a right side view of a closure EAP lockout mechanism including an EAP actuator housed in a left side of a handle housing aligned to enter and lock a closure yoke, preventing closing and thus firing of an end effector of a surgical stapling and severing instrument.
Figure 14:
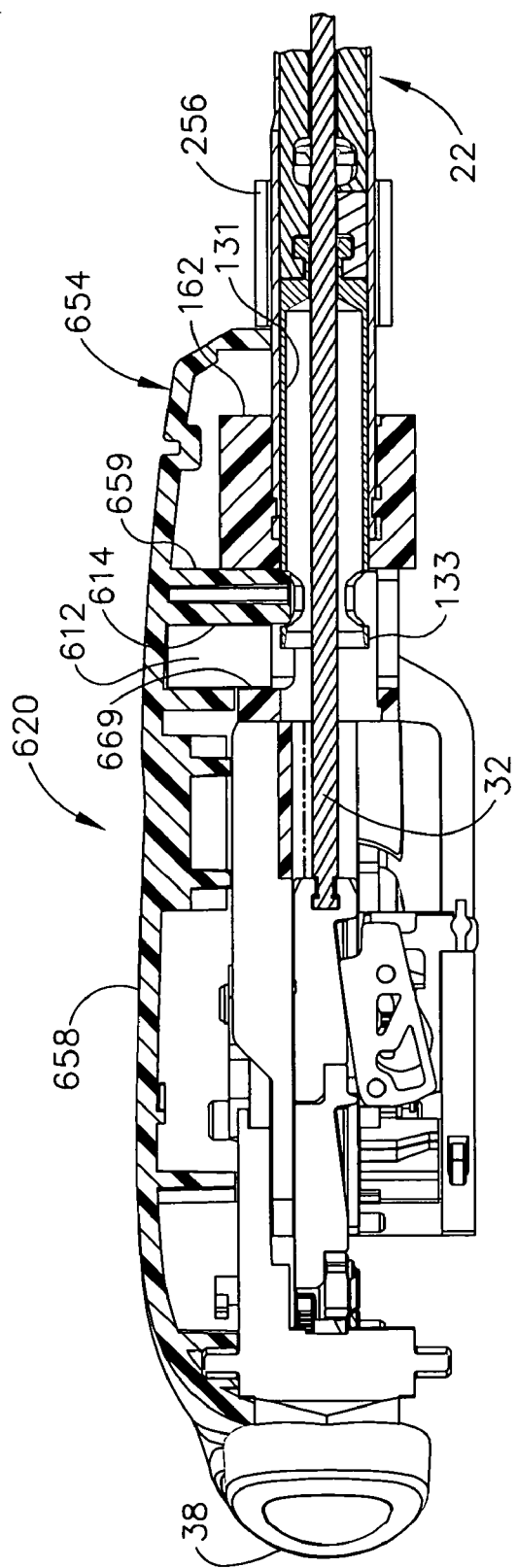
FIG. 14 is a top view of the handle of FIG. 13 with a right half shell of a handle housing removed and taken in horizontal cross section along lines 14—14 through a relaxed closure EAP actuator causing the closure EAP lockout mechanism to proximally lock the closure yoke, preventing closing and firing of the surgical stapling and severing instrument.
Figure 15:
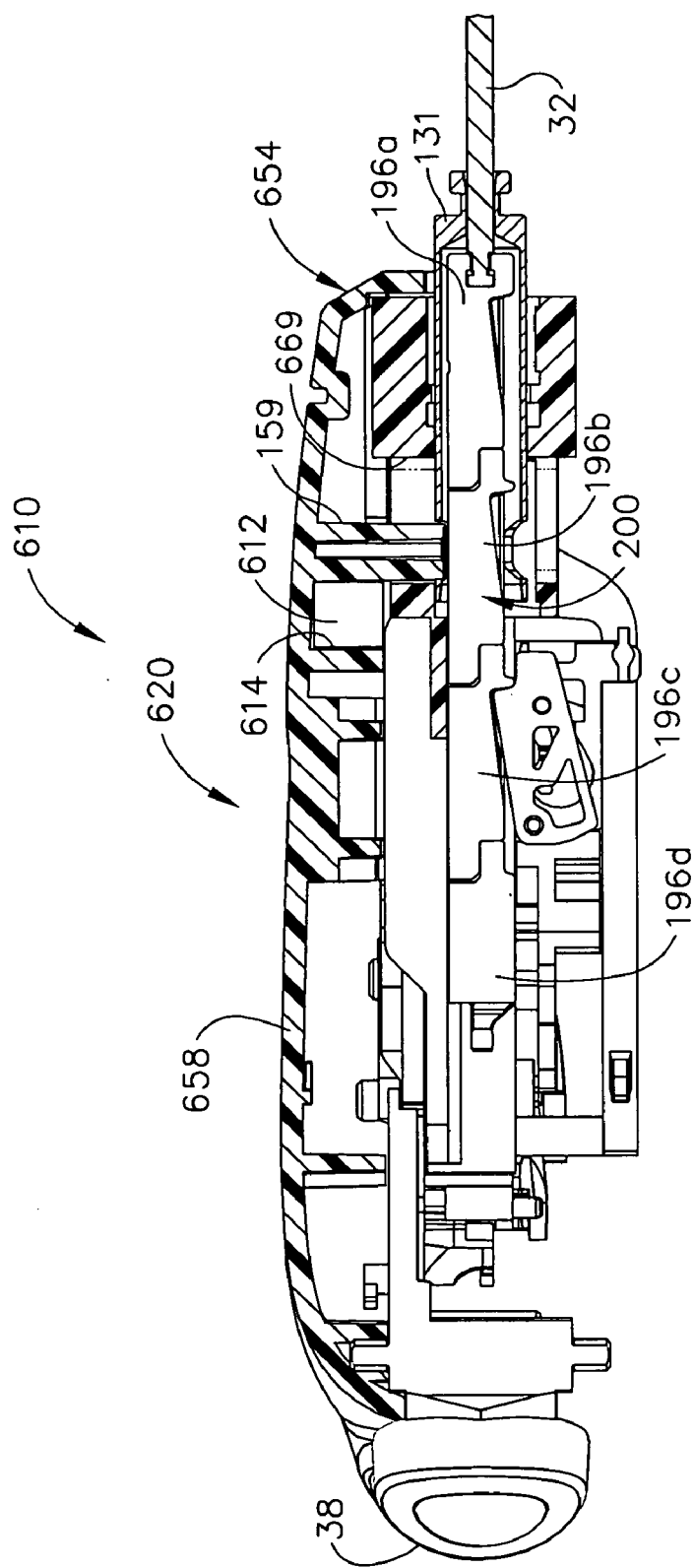
FIG. 15 is a top view of the handle of FIG. 14 with the EAP actuator activated (laterally retracted) allowing distal movement of the closure yoke to close the anvil.
Figure 16:
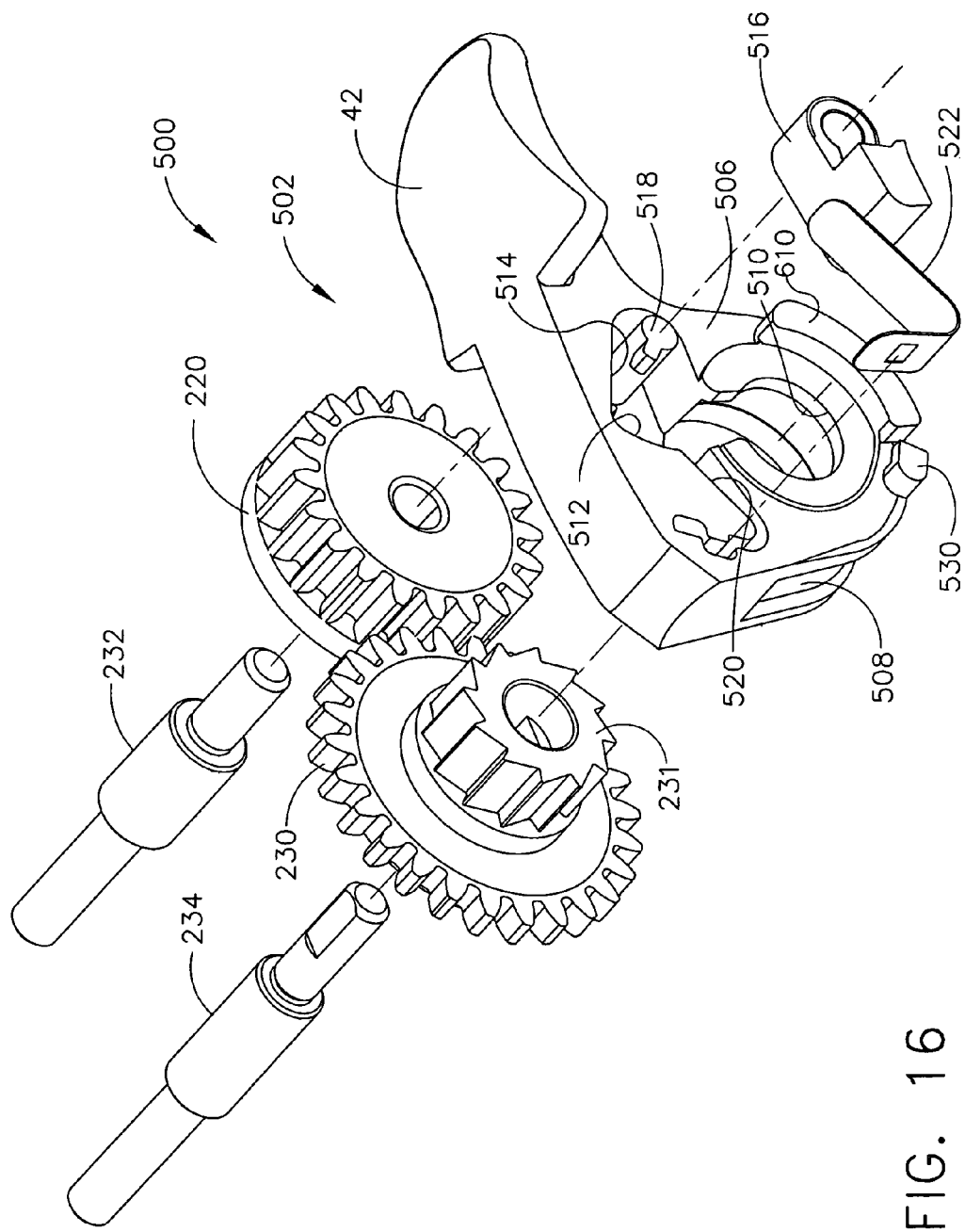
FIG. 16 is a disassembled perspective view of a manual retraction mechanism that provides firing position indication, manual release of the firing mechanism and manual retraction of the surgical stapling and severing instrument of FIG. 1.
Figure 17:
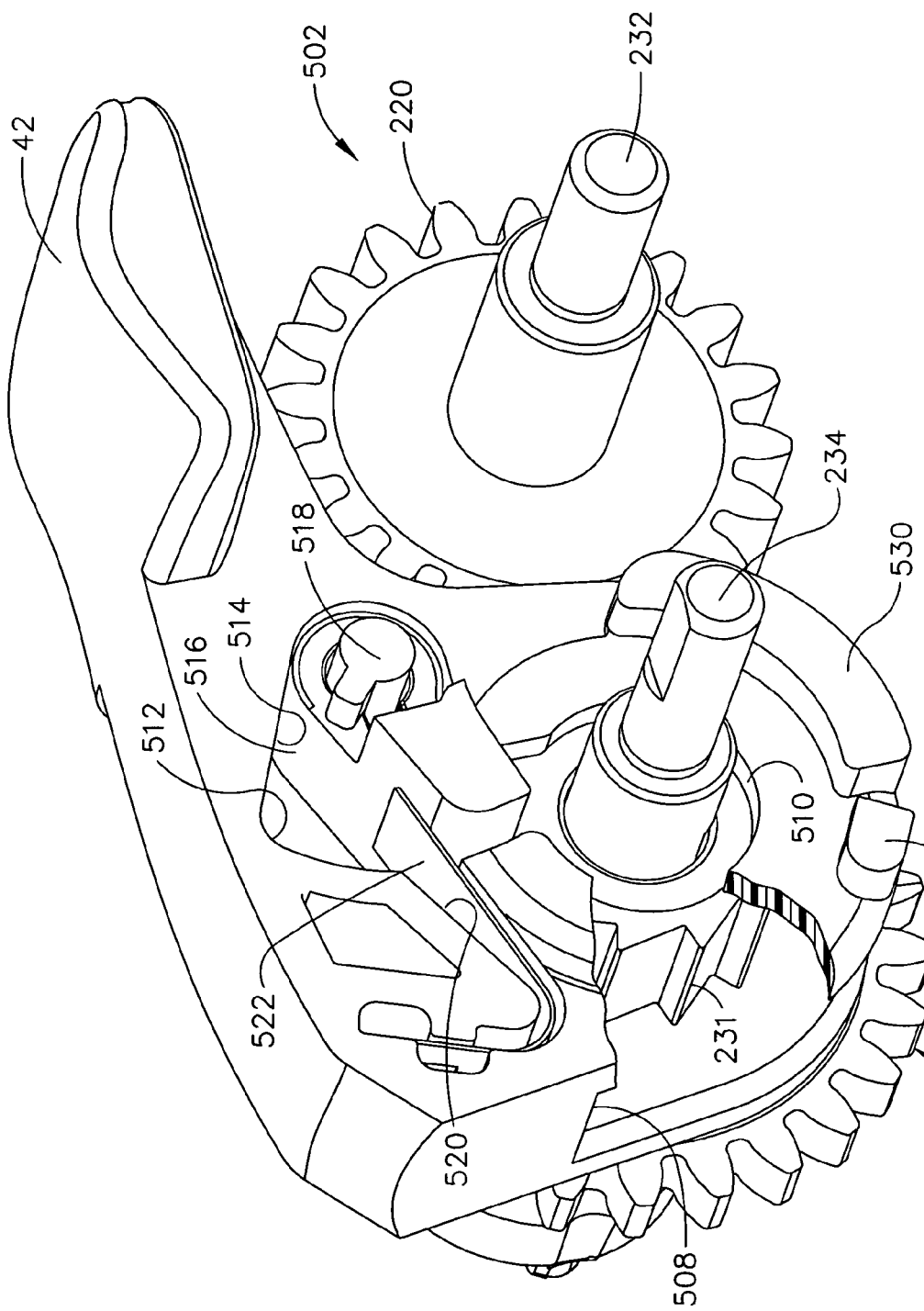
FIG. 17 is a perspective view of the manual retraction mechanism of FIG. 16.

In FIGS. 13–15, an alternate blocking lockout mechanism 600 may be incorporated into a surgical stapling and severing instrument 610 identical to that described above, but with the addition of an EAP actuator 612 contained within a recess 614 in a left half shell 658 of a handle housing 654 of a handle 620. The left half shell 658 includes the closure yoke guide post 159 that slides with a horizontally elongate rectangular aperture 669 formed in a left side of the closure yoke 162, with the guide post 159 at a distal position in the aperture 669 as in FIG. 14 when the closure yoke 162 is proximally positioned with anvil 14 open. The guide post 159 projects inwardly to engage the coupling tube 131 whose proximally open cavity receives links 196a, 196b (FIG. 15). In FIG. 14, the EAP actuator 612 is in its laterally extended, inactivated state engaged within the horizontally elongate rectangular aperture 669 aft of the guide post 659. Thus, the closure yoke 162 is locked in its proximally retracted position. In FIG. 15, the EAP actuator 612 is activated, contracting to the left out of the rectangular aperture 669 in the closure yoke 162, which has been distally advanced to close the anvil 14 (not shown in FIGS. 13–15).

It should be appreciated that many laparoscopic or endoscopic surgical instruments include at least one movable member in the handle that may be modified to include an aperture or similar engaging feature to transversely receive an EAP locking mechanism. Thus, while a surgical stapling and severing instrument benefits from such a lockout, many other types of instruments would benefit.

Manual Retraction of Multiple-Stroke Firing Mechanism.

As also described in the afore-mentioned U.S. patent application Ser. Nos. 11/052,387 and 11/052,632, in FIGS. 3, 5, and 16–21, the surgical stapling and severing instrument 10 includes a manual retraction mechanism 500 that provides firing position indication, manual release of the firing mechanism, and manual retraction. A gear mechanism 502 also functions to visually indicate progress of firing travel and to manually retract the knife. A front idler gear 220 engages a toothed upper, left surface 222 of the linked rack 200 (FIGS. 3, 18–20). The front idler gear 220 also engages an aft idler gear 230 having a smaller right-side ratchet gear 231. Both the front idler gear 220 and aft idler gear 230 are rotatably connected to the handle housing 154 respectively on front idler axle 232 and aft idler axle 234. Each end of the aft axle 232 extend through the respective right and left housing half shells 156, 158 and are attached to the left and right indicator gauge wheels 40, 41. Since the aft axle 234 is free spinning in the handle housing 154 and has a keyed engagement to the aft gear 230, the indicator gauge wheels 40, 41 rotate with the aft gear 230. The gear relationship between the linked rack 200, idler gear 220 and aft gear 230 may be advantageously selected so that the toothed upper surface 222 has tooth dimensions that are suitably strong and the aft gear 230 makes no more than one revolution during the full firing travel of the linked transmission firing mechanism 150.

Figure 19:
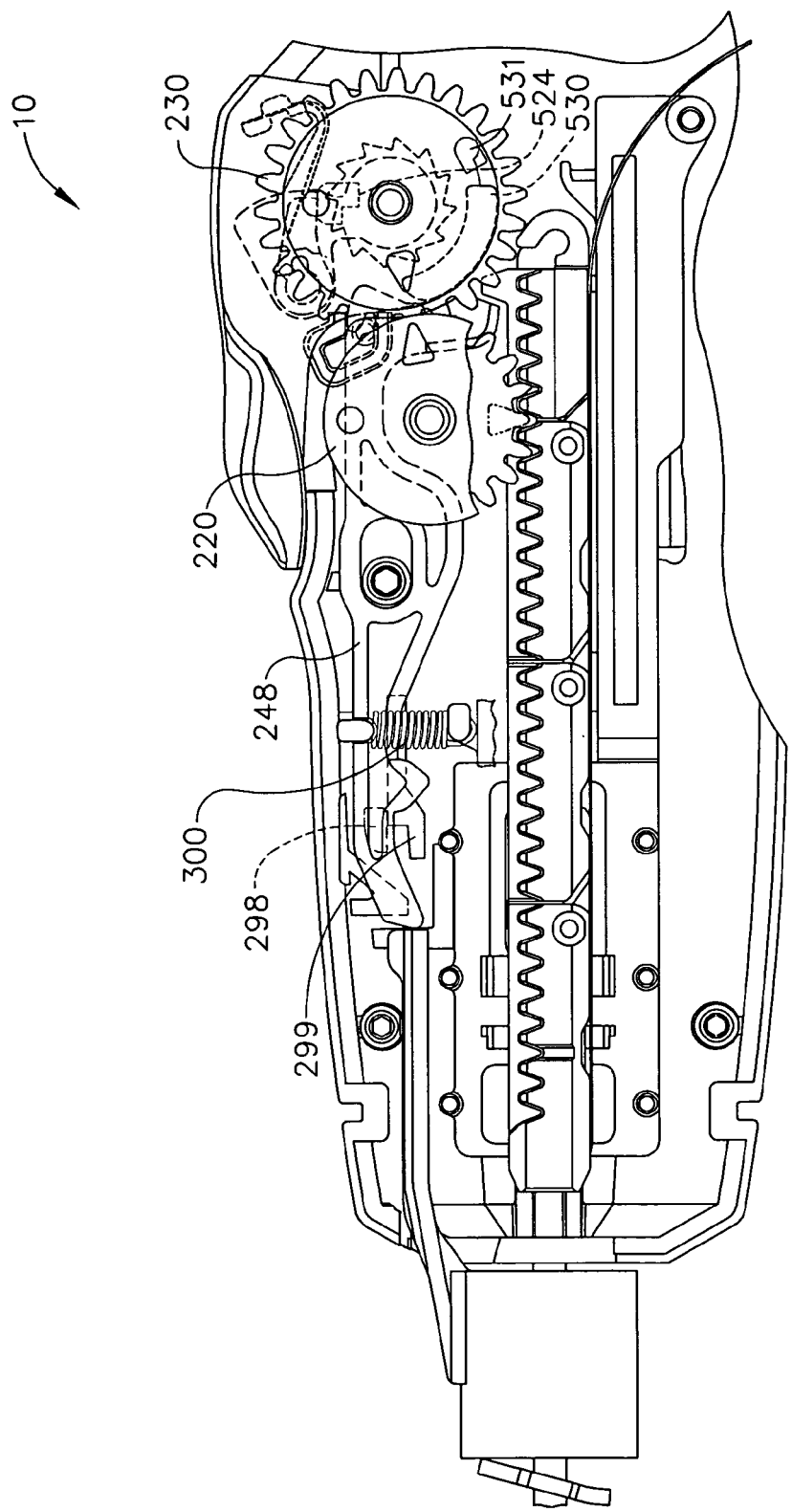
FIG. 19 is a left side detail view of the handle of FIG. 1 with a left half shell of the handle housing and components for closure and firing removed to expose the manual retraction mechanism, linked rack and anti-backup mechanism.

The smaller right-side ratchet gear 231 of the aft idler gear 230 extends into a hub 506 of the manual retraction lever 42, specifically aligned with a vertical longitudinally-aligned slot 508 (FIG. 16) bisecting the hub 506. A lateral through hole 510 of the hub 506 communicates with an upper recess 512. A front portion 514 is shaped to receive a proximally directed locking pawl 516 that pivots about a rightward lateral pin 518 formed in a distal end of the upper recess 512. An aft portion 520 is shaped to receive an L-shaped spring tab 522 that urges the locking pawl 516 downward into engagement with the right-side smaller ratchet gear 231. A hold-up structure 524 (FIG. 19) projects from the right half shell 156 into the upper recess 512 holding up the locking pawl 516 from engaging the smaller right-side ratchet gear 231 when the manual retraction lever 42 is down (FIG. 19). A coil spring 525 (FIG. 3) urges the manual retraction lever 42 down.

Figure 18:
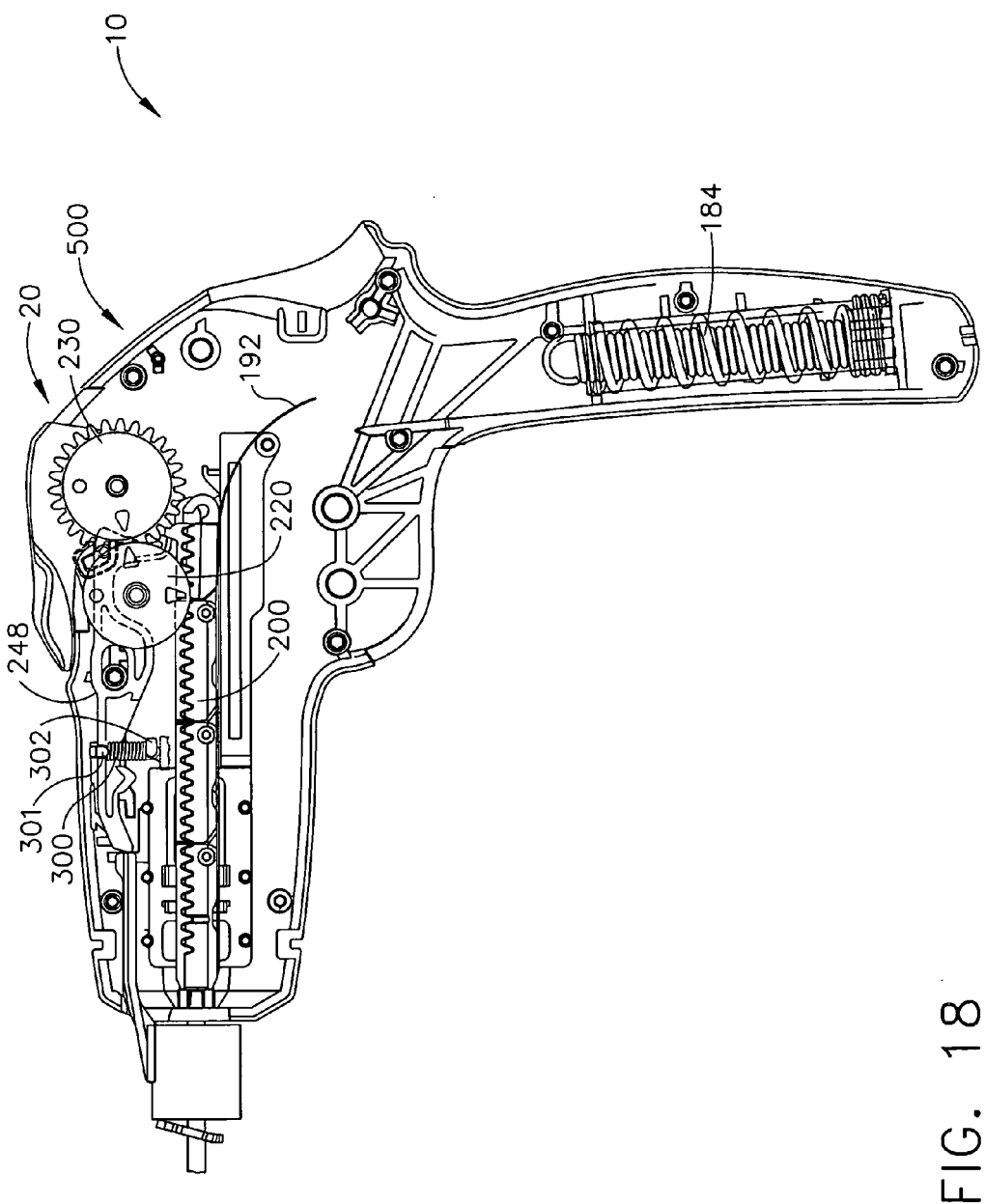
FIG. 18 is a left side view in elevation of a handle of the surgical stapling and severing instrument of FIG. 1 partially disassembled to expose a detached retraction spring and the manual retraction mechanism.
Figure 20:
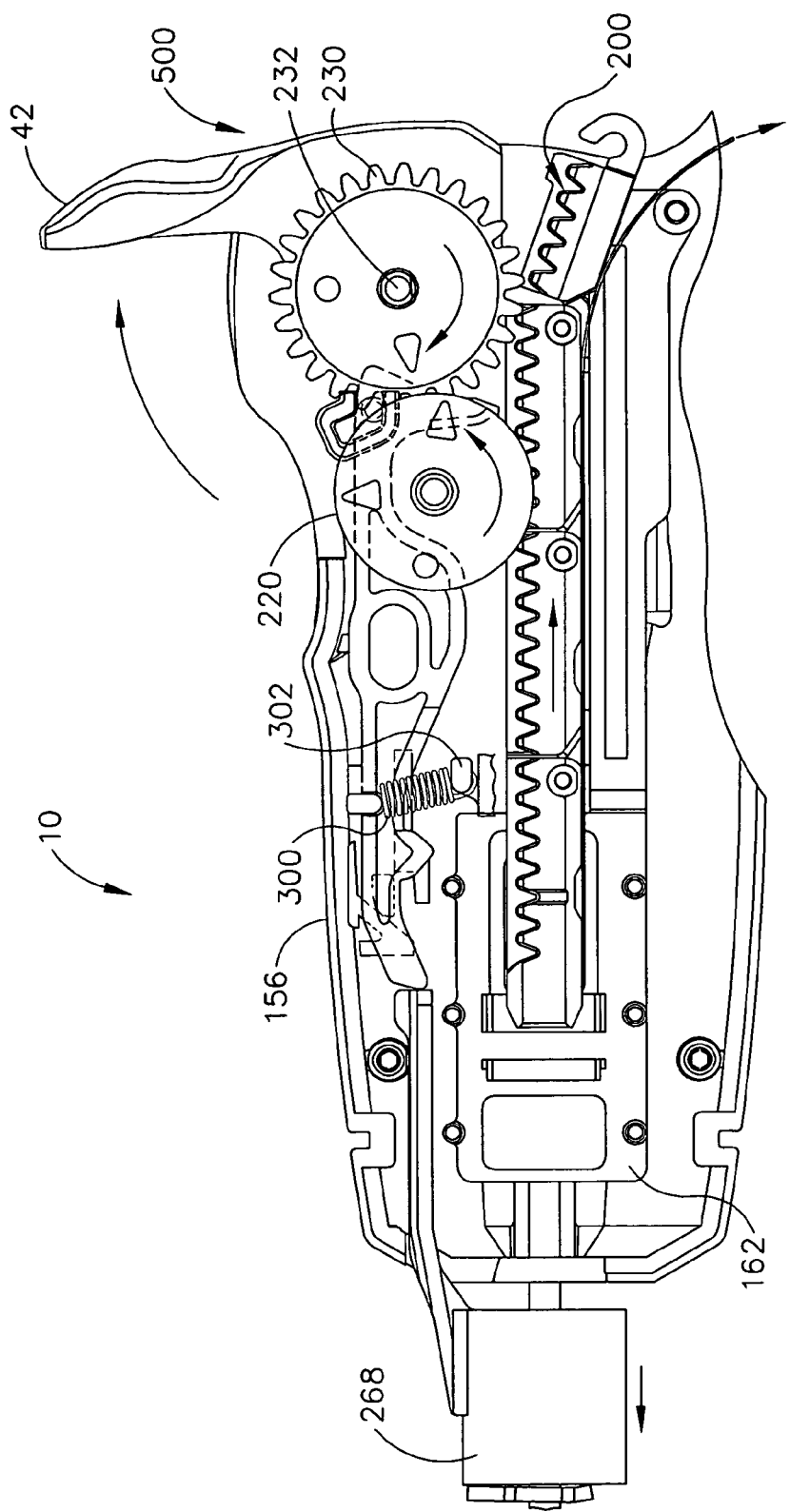
FIG. 20 is a left side detail view of the partially disassembled handle of FIG. 19 with a manual retraction lever actuated proximally.
Figure 21:
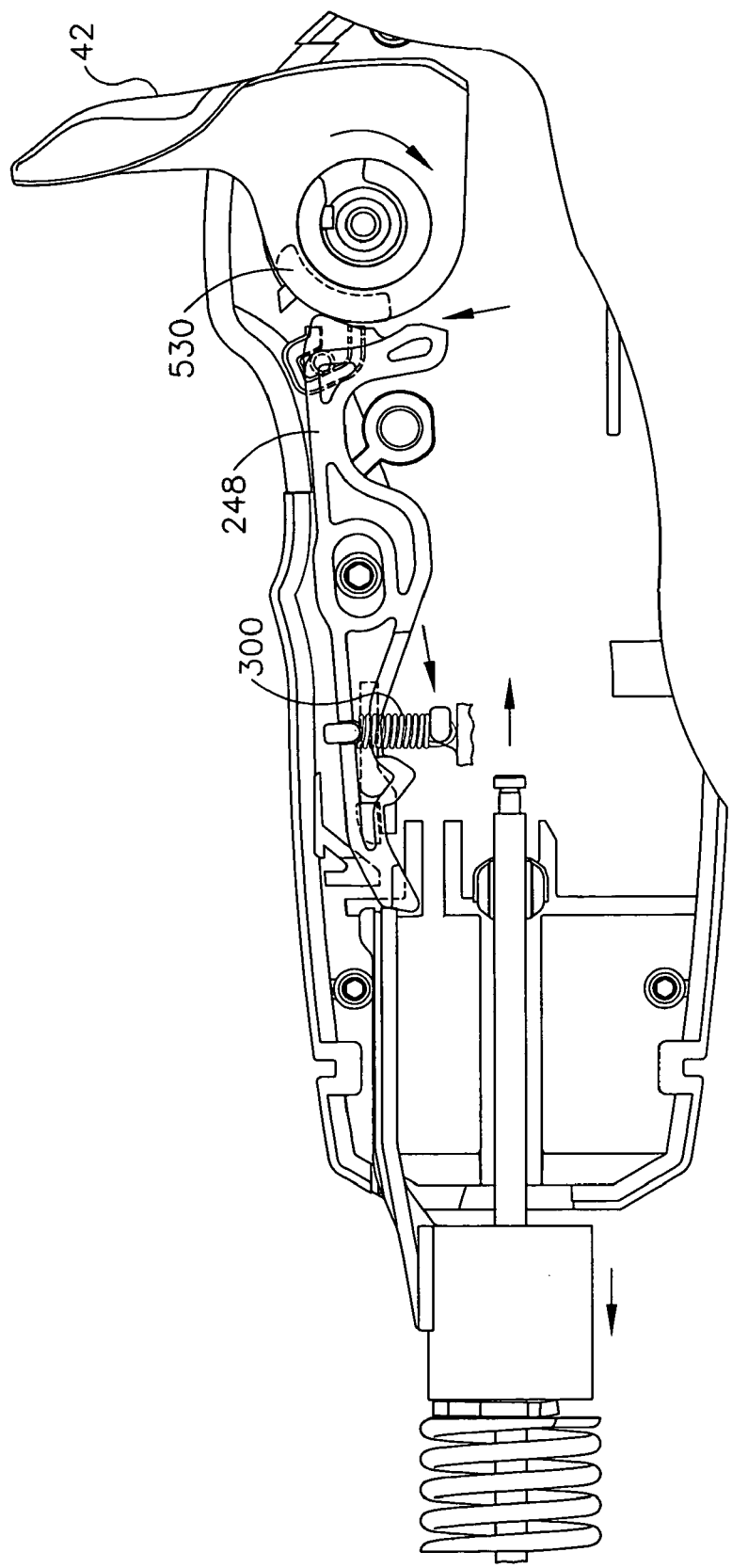
FIG. 21 is a left side detail view of the partially disassembled handle of FIG. 20 with interaction with contacting surfaces between an anti-backup release lever and the manual retraction mechanism depicted in phantom.

In use, as depicted in FIGS. 18–19, the combination tension/compression spring 184 may become disconnected with the linked rack distally positioned. In FIGS. 20–21, as the manual retraction lever 42 is raised, the locking pawl 516 rotates clockwise, no longer is held up by the hold-up structure 524 and engages the smaller right-side ratcheting gear 231, rotating the aft idler gear 230 clockwise when viewed from the left. Thus, the forward idler gear 220 responds counterclockwise retracting the linked rack 200. In addition, a rightward curved ridge 530 projects out from the hub 506, sized to contact and distally move the anti-backup release lever 248 to release the anti-backup mechanism 250 as the manual retraction lever 42 is rotated until contacting a stop 531.

EAP Firing Lockout Mechanism in Manual Retraction Mechanism.

Figure 22:
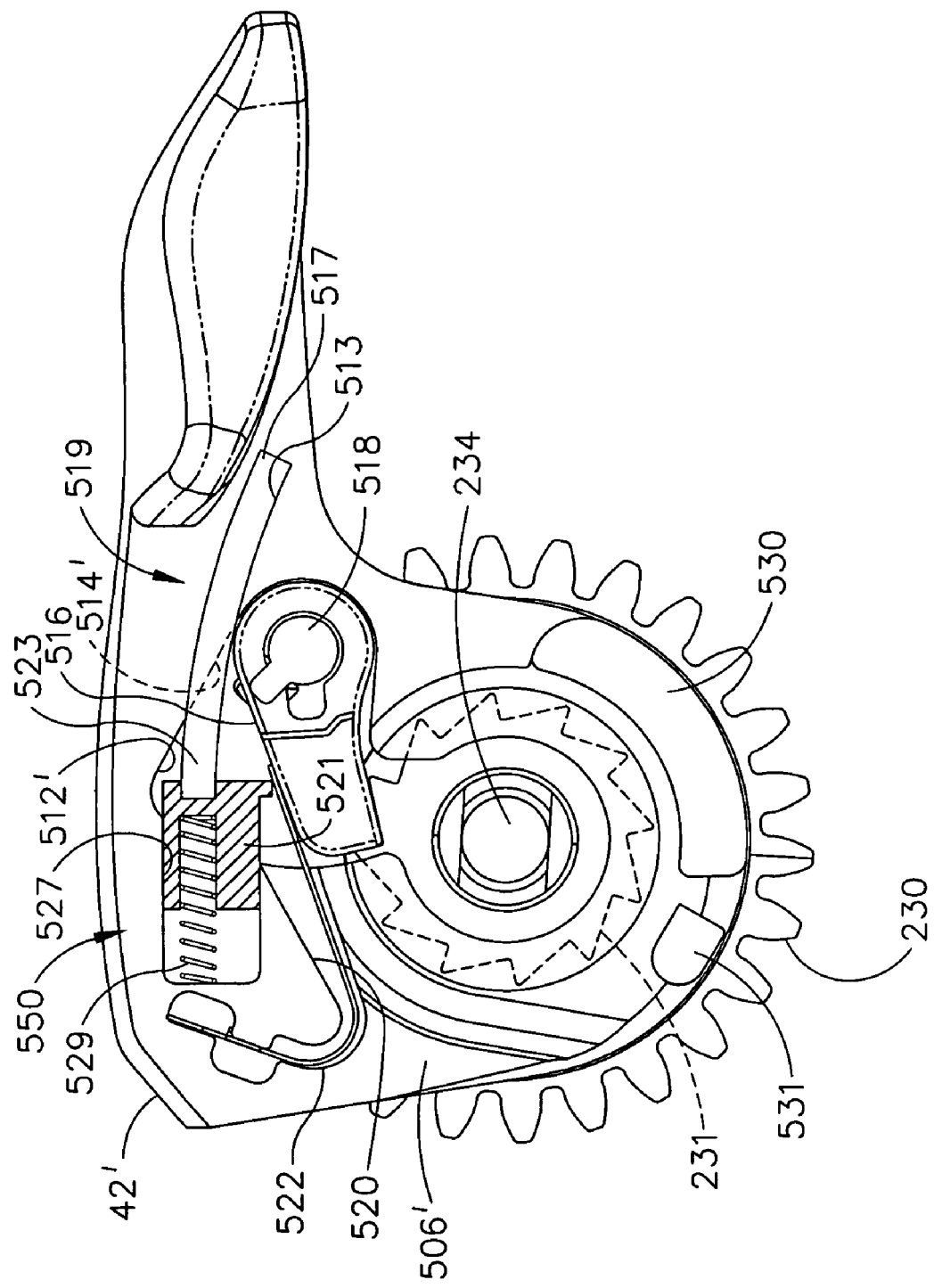
FIG. 22 is a right side view of an alternative manual retraction mechanism for the surgical stapling and severing instrument of FIG. 1 incorporating an EAP lockout mechanism depicted in a deactivated, locking condition.
Figure 23:
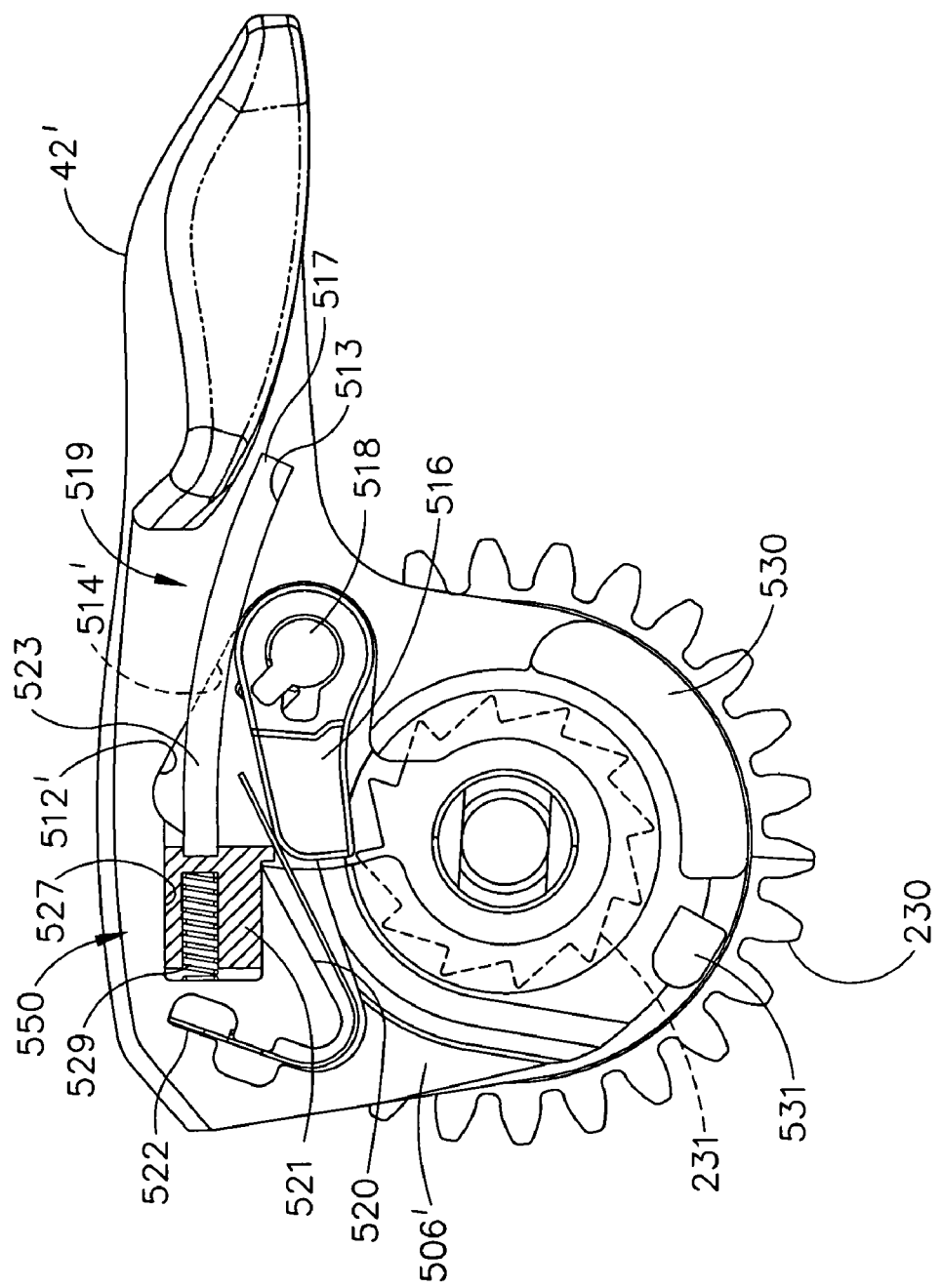
FIG. 23 is a right side view of the alternative manual retraction mechanism of FIG. 22 with the EAP lockout mechanism activated to an unlocked condition allowing firing and manual release.

In FIGS. 22–23, an EAP lockout mechanism 550 is advantageously incorporated into a modified hub 506' of a manual retraction lever 24'. A distal side of an upper recess 514' is shaped into a slot 513 to receive a held end 517 of an EAP locking member 519 and a proximal side of the upper recess 512' is shaped into an actuator recess 527 to receive a locking plunger 521 that abuts a free end 523 of the EAP locking member 519. An opposing compression spring 529 urges the locking plunger 521 distally out of the actuator recess 527, as depicted in FIG. 22 when the EAP locking member 519 is deactivated. The locking plunger 521 forces the L-shaped spring tab 522 and the locking pawl 516 downward into engagement with the right-side smaller ratchet gear 231, preventing firing. Advantageously, the surgeon may manually retract the firing mechanism although further firing is locked out. In FIG. 23, the EAP locking member 519 is activated, expanding proximally, forcing the locking plunger 521 proximally into the actuator recess 527, allowing the locking pawl 516 to ratchet up against the L-shaped spring tab 522 and thus allowing firing.

Firing Trigger EAP Locking Mechanism.

Figure 24:
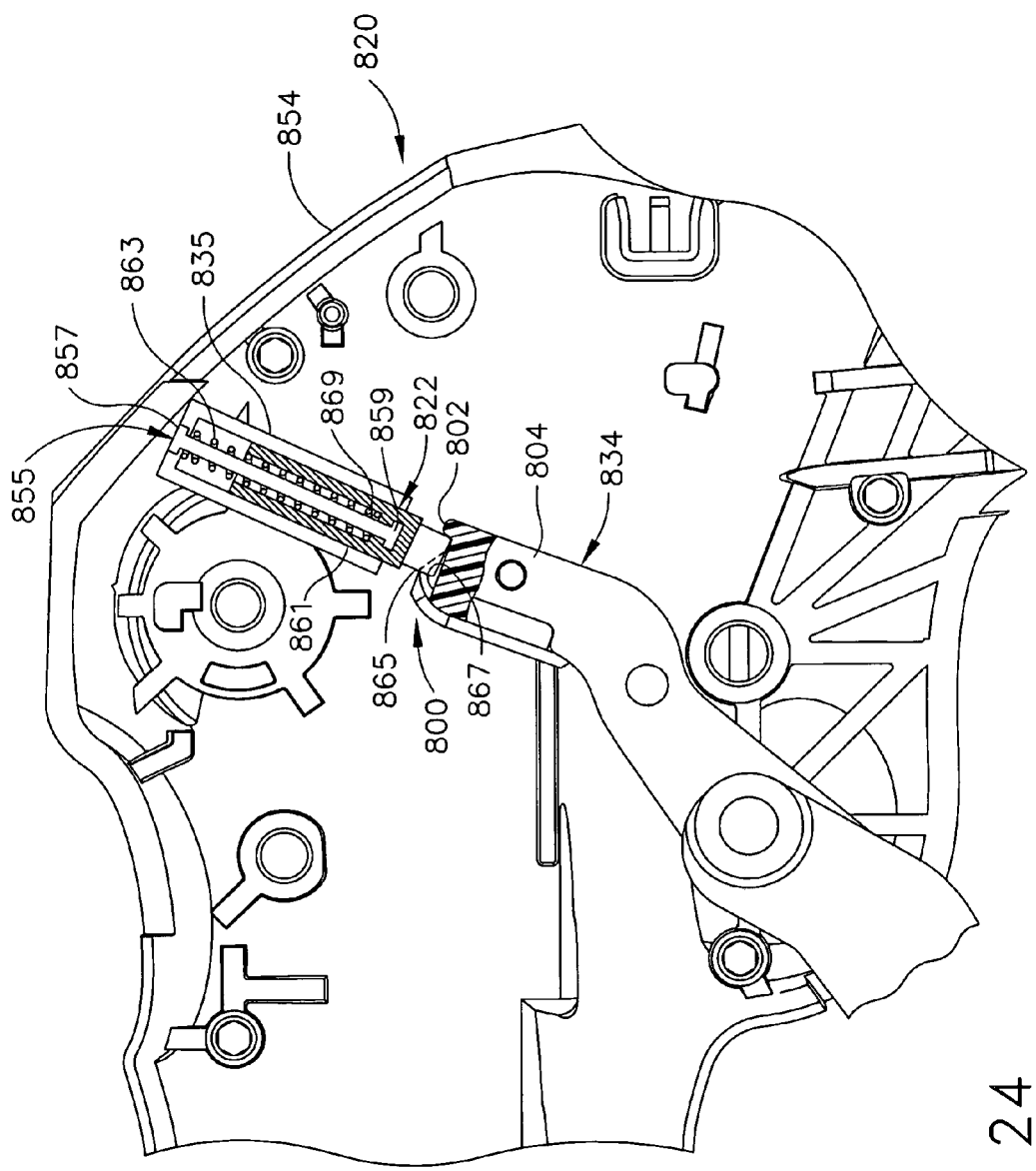
FIG. 24 is a left side view of a portion of an alternative handle partially disassembled to expose a firing trigger EAP lockout mechanism in a deactivated, locked condition for the surgical stapling and severing instrument of FIG. 1.
Figure 25:
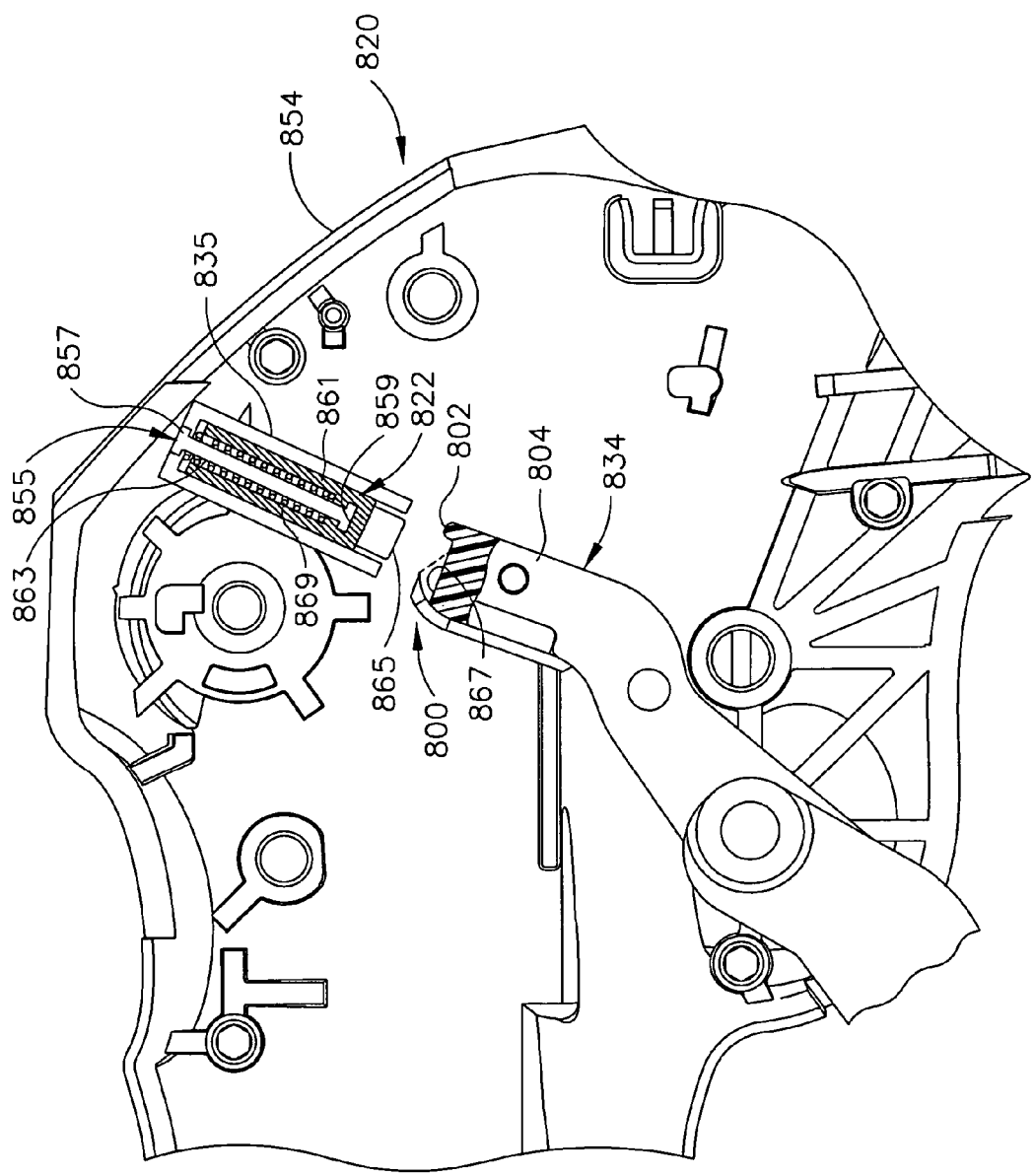
FIG. 25 is a left side view of the EAP lockout mechanism of FIG. 24 deactivated and unlocked allowing depression of the firing trigger.
Figure 26:
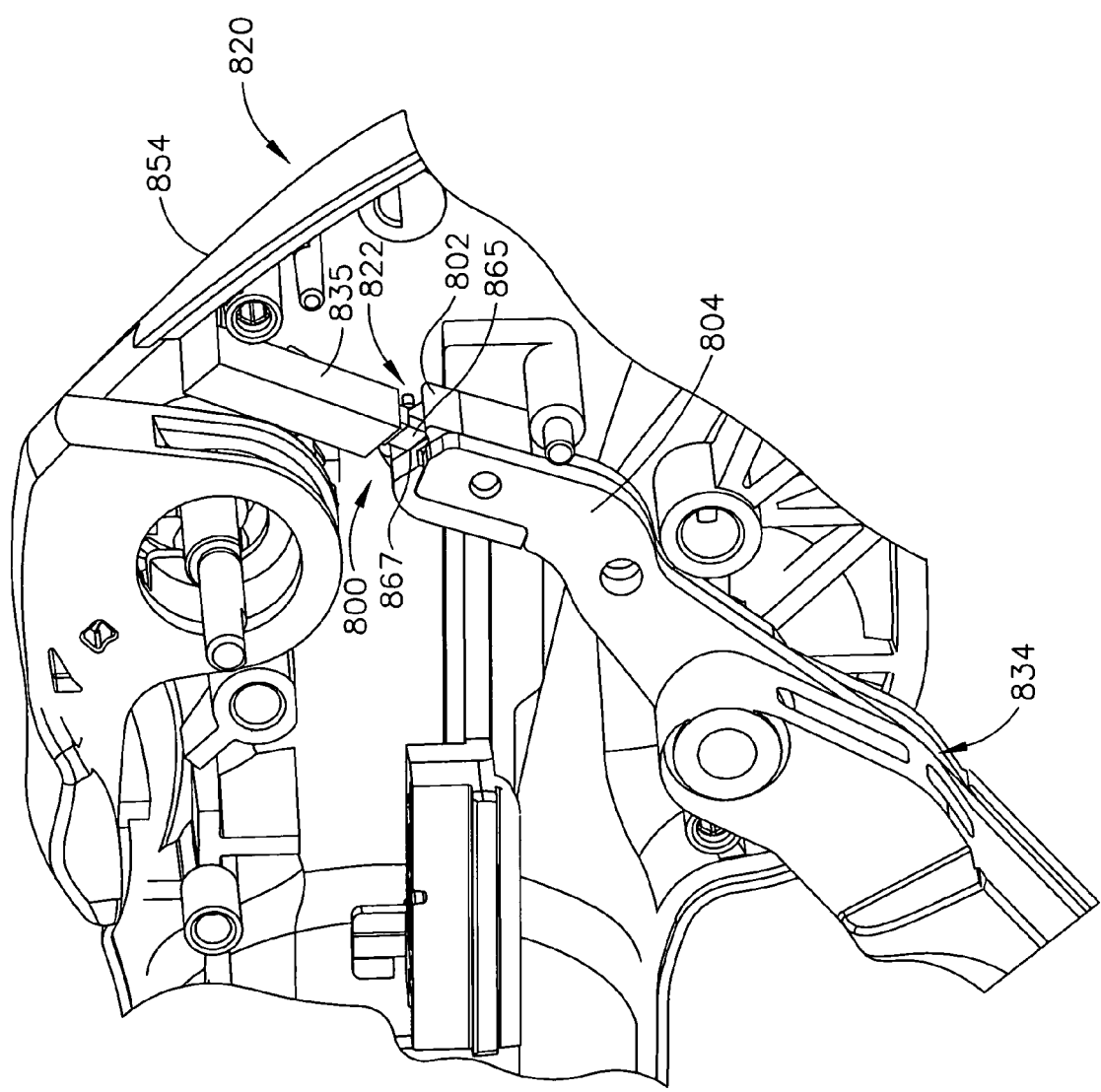
FIG. 26 is an aft perspective view of the EAP lockout mechanism of FIG. 24.
Figure 28:
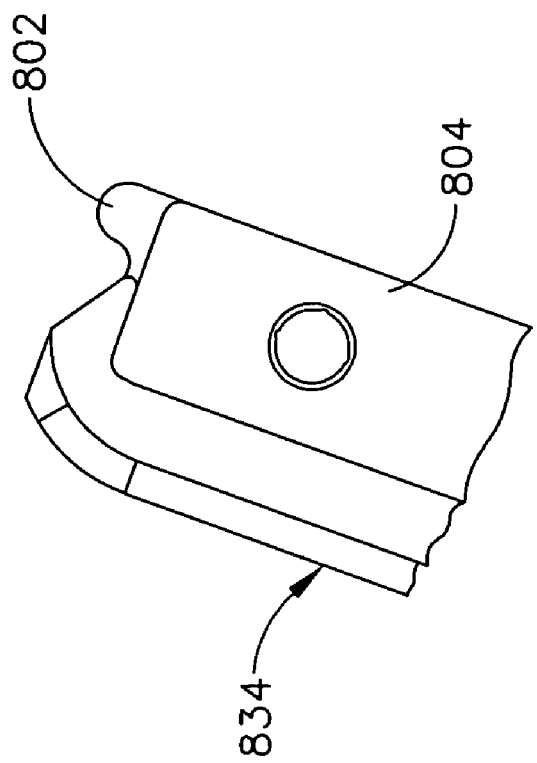
FIG. 28 is a left side of the upper portion of the alternative firing trigger of FIG. 27.
Figure 27:
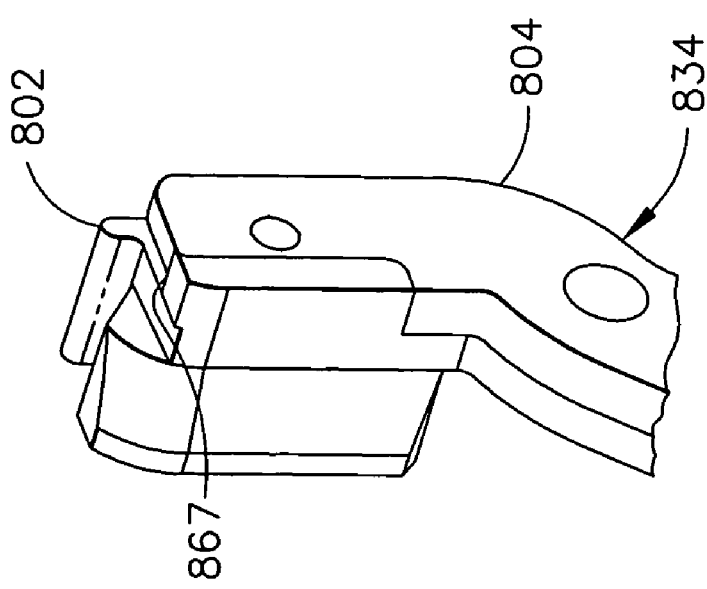
FIG. 27 is a front perspective view of an upper portion of the alternative firing trigger of FIG. 24.

In FIGS. 24–28, an EAP locking mechanism 800 is advantageously incorporated into a handle 820 to lock an EAP locking actuator 822 against a locking ridge 802 formed in an upper end 804 of a firing trigger 834. The EAP locking actuator 822 is constrained to move downwardly and slightly distally by an actuator guide 835 formed in a handle housing 854. In FIGS. 24–25, the EAP actuator 822 is comprised of an EAP member 855 that has a fixed end 857 held in a top end of the actuator recess 835 with a moving end 859 held in an actuator piston 861. A compression spring 863, which encompasses the EAP member 855, has an upper end 865 abutting the upper end of the actuator recess 835 and a lower end 869 abutting the actuator piston 861. A hard tip 865 is attached to an exposed end of the actuator piston 861 to correspond to a recessed surface 867 adjacent to the locking ridge 802 of the firing trigger 834. The EAP member 855 is normally expanded, as depicted in FIGS. 24, 26, with this hard tip 865 abutting the recessed surface 867 blocking forward rotation of the locking ridge 802 of the firing trigger 834. In FIG. 25, the EAP member 855 is contracted, pulling up the actuator piston 861 and hard tip 865 and compressing the spring 863, thus allowing depression of the firing trigger 834.

It should be appreciated that a similar EAP locking mechanism may be incorporated into a closure trigger for surgical stapling and severing instruments that present two triggers instead of one that performs both functions.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

It will be appreciated that the terms "proximal" and "distal" are used herein with reference to a clinician gripping a handle of an instrument. Thus, the end effector 12 is distal with respect to the more proximal handle 20. Analogous terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these terms are not intended to be limiting and absolute.

The present invention is being discussed in terms of laparoscopic and endoscopic procedures and apparatus. However, use herein of terms such as "endoscopic" should not be construed to limit the present invention to a surgical stapling and severing instrument for use only in conjunction with a laparoscopic cannula (i.e., trocar). On the contrary, it is believed that the present invention may find use in any procedure where access is limited to a small incision, including but not limited to other laparoscopic procedures, as well as open procedures.

Applications consistent with the present invention may include a solid firing rack rather than a linked rack.

The linked rack 200 serves as a proximal engaging portion of a firing member that actuates the implement portion 22. It should be appreciated that a frictional engagement may be used instead of a spring-biased side pawl assembly 285, such as described in co-pending and commonly-owned U.S. patent application Ser. No. 10/673,662 to Jeffrey S. Swayze, et al., entitled "SURGICAL STAPLING INSTRUMENT HAVING MULTISTROKE FIRING INCORPORATING A TRACTION-BIASED RACHETING MECHANISM", the disclosure of which is hereby incorporated by reference in its entirety.

In addition, the orientation of the side pawl assembly 285 to a linked rack 200 to its left is illustrative. It should be appreciated that a linked or solid rack may be oriented above, below, or to the right of a selectively engaging member coupled to a firing trigger (e.g., spring biased pawl, traction biased member).

In the above-described versions, a side pawl is spring biased into engagement with the rack 200 but held out of engagement during proximal movement when the firing trigger is released. A spring biases the pawl slide to avoid engagement unless overcome by the EAP lockout actuator. It should also be appreciated that applications consistent with the present invention may include an EAP lockout actuator that biases a pawl into engagement with a rack of a firing mechanism. Thus, a pawl may be biased out of engagement. A sensor coupled to a firing trigger enables an EAP lockout actuator, when the firing trigger is sensed, from being depressed and not released. The EAP lockout actuator is activated (optionally with other preconditions met) urging the pawl into engagement with the rack.

In the above-described versions, a rack and pawl engagement is advantageously described as providing a strong transfer of firing motion from a firing trigger to a firing bar. It should be appreciated that applications consistent with the present application may include a frictional engagement between a proximal portion of a firing member and a firing actuator such as a firing trigger. An EAP lockout actuator may prevent binding contact by effecting spacing or preventing a binding deflection (e.g., screen door damper lock).

While it is desirable in many applications for a lockout to default to a locked condition, even in an unpowered or failed condition, it should be appreciated that applications consistent with the present invention may include a lockout mechanism that is electrically actuated that defaults to an unlocked state, especially if power is required for the firing action that is being prevented by the locking mechanism to occur. As yet a further alternative, a bi-stable lock may remain in either a locked or an unlocked state until an electrically-powered actuator toggles the state of the locking mechanism.

As another example, the lockout mechanism may comprise an EAP actuator positioned on an opposite side of the pawl slide from the rack to push the pawl slide toward a rack. Further, this EAP actuator may be attached to the pawl slide or to a relatively stationary part of the handle adjacent to the pawl slide.

As yet another example, a bias of the lockout mechanism urging the proximal engaging portion of the firing member (e.g., rack) away from the engagement mechanism (e.g., pawl/pawl slide) may comprise a resilient strip of material affixed to an inner surface of the proximal engaging portion of the firing member and/or the engagement mechanism.

While an electroactive polymer has a number of benefits, in some applications consistent with the present invention, an electrically powered actuator may be substituted, such as a solenoid.

What is claimed is:

1. A surgical instrument, comprising:
   an elongate shaft;
   a control member received for movement in the elongate shaft;
   an end effector operatively configured to actuate in response to a received control motion from the control member;
   a handle proximally attached to the elongate shaft to position the end effector through a surgical opening;
   a control actuator attached for movement to the handle and coupled to the control member, the control actuator operatively configured to move from a first position to a second position to produce the control motion upon an user input;
   control circuitry operatively configured to generate an enabling signal; and
   an electrically powered actuator biased into locking contact with the control actuator in the first position to prevent movement to the second position and biased to be responsive to the enabling signal to unlock from the control actuator.

2. The surgical instrument of claim 1, wherein the electrically powered actuator comprises an electroactive polymer (EAP) actuator.

3. The surgical instrument of claim 1, wherein the control actuator comprises a trigger.

4. The surgical instrument of claim 1, wherein the control actuator comprises a longitudinally reciprocating member including a locking aperture, the electrically powered actuator comprising a locking bolt, spring biased into insertion through the locking aperture.

5. The surgical instrument of claim 4, wherein the electrically powered actuator further comprises an electroactive polymer operatively configured to retract the locking bolt from the locking aperture.

6. The surgical instrument of claim 1, wherein the control actuator further comprises a rack, the surgical instrument further comprising a manual retraction lever coupled by a ratchet mechanism to the rack, the electrically powered actuator comprising a pawl lock precluding ratcheting.

* * * * *